United States Patent
Spector et al.

(10) Patent No.: US 7,286,997 B2
(45) Date of Patent: Oct. 23, 2007

(54) INTERNET-BASED, CUSTOMIZABLE CLINICAL INFORMATION SYSTEM

(75) Inventors: Mark B. Spector, Cincinnati, OH (US); Michael N. Neuss, Wyoming, OH (US); Richard L. Levy, Cincinnati, OH (US); Stanley R. Fortson, Jr., Cincinnati, OH (US)

(73) Assignee: CEMBEX Care Solutions, LLC, Cincinnati, OH (US)

( * ) Notice: Subject to any disclaimer, the term of this patent is extended or adjusted under 35 U.S.C. 154(b) by 313 days.

(21) Appl. No.: 10/431,630

(22) Filed: May 7, 2003

(65) Prior Publication Data

US 2004/0024616 A1    Feb. 5, 2004

Related U.S. Application Data

(60) Provisional application No. 60/378,245, filed on May 7, 2002.

(51) Int. Cl.
G06Q 10/00 (2006.01)
G06Q 50/00 (2006.01)
A61B 5/00 (2006.01)
G06F 19/00 (2006.01)

(52) U.S. Cl. ............................................. 705/2; 705/3

(58) Field of Classification Search .................... 705/2, 705/3; 600/300; 709/238
See application file for complete search history.

(56) References Cited

U.S. PATENT DOCUMENTS

| | | | |
|---|---|---|---|
| 4,730,849 A * | 3/1988 | Siegel | ........................ 283/70 |
| 5,812,983 A | 9/1998 | Kumagai | |
| 5,823,948 A | 10/1998 | Ross, Jr. et al. | |
| 5,851,186 A | 12/1998 | Wood et al. | |
| 5,924,074 A | 7/1999 | Evans | |
| 5,950,630 A | 9/1999 | Portwood et al. | |
| 6,018,713 A | 1/2000 | Coli et al. | |
| 6,022,315 A | 2/2000 | Iliff | |
| 6,026,363 A | 2/2000 | Shepard | |

(Continued)

FOREIGN PATENT DOCUMENTS

WO    WO 2005120097 A2 *  12/2005

OTHER PUBLICATIONS

Grossman, Plugged-in medicine, Jan. 1994, Technology Review, vol. 97 No. 1, pp. 22-29.*

*Primary Examiner*—C. Luke Gilligan
(74) *Attorney, Agent, or Firm*—Taft Stettinius & Hollister LLP

(57) ABSTRACT

An Internet-based, or Web-based, customizable clinical (patients' records and care) information system ("CIS") is provided. More specifically, the clinical information system is Web/Internet based, whether it utilizes a browser-type user interface or a distributed application-type user interface; the clinical information system may include automatic disease staging and associated treatment planning and/or scheduling; the clinical information system may track certain events/submissions and sort such events/submissions into a physician's in-box for on-line approval by the physician, where such approval causes the event/submission to become an addendum to the patient's record; the clinical information system may be customizable by an administrator; the clinical information system may establish, and make available for on-line review and approval, patient care or standing orders over a weekend; the clinical information system may utilize patients' photographs to ensure accurate identification and proper treatment; and the clinical information system may create and store an audit trail record for all significant events.

28 Claims, 28 Drawing Sheets

U.S. PATENT DOCUMENTS

| | | |
|---|---|---|
| 6,076,166 A | 6/2000 | Moshfeghi et al. |
| 6,108,635 A * | 8/2000 | Herren et al. .................. 705/2 |
| 6,206,829 B1 | 3/2001 | Iliff |
| 6,260,021 B1 | 7/2001 | Wong et al. |
| 6,264,614 B1 | 7/2001 | Albert et al. |
| 6,272,468 B1 | 8/2001 | Melrose |
| 6,292,783 B1 | 9/2001 | Rohler et al. |
| 6,302,844 B1 | 10/2001 | Walker et al. |
| 6,305,377 B1 | 10/2001 | Portwood et al. |
| 6,317,719 B1 * | 11/2001 | Schrier et al. ................ 705/2 |
| 6,347,329 B1 * | 2/2002 | Evans ....................... 709/202 |
| 6,532,399 B2 * | 3/2003 | Mase ....................... 700/237 |
| 6,651,060 B1 * | 11/2003 | Harper et al. ................ 707/9 |
| 7,028,049 B1 * | 4/2006 | Shelton .................. 707/104.1 |
| 2001/0023316 A1 | 9/2001 | Albert et al. |
| 2001/0029322 A1 | 10/2001 | Iliff |
| 2001/0032100 A1 | 10/2001 | Mahmud et al. |
| 2001/0039504 A1 | 11/2001 | Lindberg et al. |
| 2001/0041991 A1 | 11/2001 | Segal et al. |
| 2001/0041992 A1 | 11/2001 | Lewis et al. |
| 2001/0044586 A1 | 11/2001 | Ferek-Petric |
| 2001/0044588 A1 | 11/2001 | Mault |
| 2001/0044823 A1 | 11/2001 | Labounty et al. |
| 2002/0019749 A1 | 2/2002 | Becker et al. |
| 2002/0145634 A1 * | 10/2002 | Gueramy et al. .......... 345/840 |

* cited by examiner

| View Medication -- Web Page Dialog |||||
|---|---|---|---|---|
| Patient: | Aarden, Tom A | | Date: | 4/15/2002 |
| Physician: | Mark Spector | | Refills: | 2 |
| Drug: | Zoloft | | Strength: | 100 mg |
| Route: | orally | | Sig: | once a day |
| Dose Form: | tablet | | Duration: | 30 day(s) |
| Dose: | 100 mg | | Quantity: | 1 tab(s) |
| Pharmacy: | CVS Pharmacy | | Dispensed: | 2 |
| Pharmacy Phone: | (513) 741-4646 | | Pharmacy Contact: | Bill Cohn |
| | Substitution: ☑ PRN: ☑ Verbal Order: ☐ ||||
| Directions: | Take with water ||||
| | | | | Close |

| | | | |
|---|---|---|---|
| SUPERTracker | Patient | Date | Ordered By |
| | ▶ Aarden, Lom A [66016] | 11/19/2001 | Maier, Chris |
| | Rx: 5-Fluorouracil 10 | Strength: 50 mg / ml 250mg (5ml) | |
| | Created By: Maier, Chris | WAITING FOR APPROVAL | |
| Order In Box | ▶ Aarden, Lom A [66016] | 11/20/2001 | Maier, Chris |
| | Rx: 3% Sodium Chloride | Strength: 250ml (250ml) | |
| | Created By: Maier, Chris | WAITING FOR APPROVAL | |
| | ▶ Aarden, Lom A [66016] | 11/20/2001 | Maier, Chris |
| Rx In Box | Compound Order: | | |
| | Drug: Cimetidine | 1200 mg / 8 ml 1200mg (8ml) | |
| | Created By: Maier, Chris | WAITING FOR APPROVAL | |
| Patients | Drug: Normal Saline 100 | 25ml (25ml) | |
| Documents | Created By: Maier, Chris | WAITING FOR APPROVAL | |
| User | ▶ Aarden, Lom A [66016] | 11/20/2001 | Maier, Chris |
| Care Suite | Rx: Metoclopramide 10 | Strength: 5 mg / ml 25mg (0ml) | |
| Tools | Created By: Maier, Chris | WAITING FOR APPROVAL | |
| Pharmacy | ▶ Cahill, Michael J [37483] | 11/20/2001 | Maier, Chris |
| Admin | Rx: Tetanus Toxoid- Booster | Strength: 25ml (25ml) | |

FIG. 7

Submit Dictations (FTP to 10.100.1.32) — 222

| | User Name: | Mardis, Joe ▼ | |
|---|---|---|---|
| | Location: | Kenwood ▼ | — 224 |
| | From: | 02/19/2002 ▼ | ~ 226 |
| | To: | 02/19/2002 ▼ | ~ 228 |

| | Original File | Date | Time |
|---|---|---|---|
| 🔊 | AAAA0006 | 02/06/2002 | 11:06:00 PM |
| 🔊 | AAAA0008 | 02/06/2002 | 11:46:00 PM |

Cancel    Submit — 230

SUPERChart - Microsoft Internet Explorer

Drug Interactions For Tom Aarden

Interactions:
erythromycin prednisone: MODERATE  At least one macrolide antibiotic, erythromycin, may enhance the pharmacologic effect of some corticosteroids.  The mechanism is probably reduced metabolism of the corticosteroids.  Data are available for methylprednisolone.  Other macrolides that are expected to behave like erythromycin include clarithromycin and troleandomycin.  Azithromycin and dirithromycin are unlikely to lead to interact with the corticosteroids.  The patient should be monitored for corticosteroid toxicity during therapy.  If clinically indicated, dosages should be adjusted down.

erythromycin cimetidine: MODERATE  Concomitant use of cimetidine and erythromycin may result in higher-than-normal plasma levels of erythromycin through inhibition of erythromycin metabolism.  One small

View Test -- Web Page Dialog

| Patient | Test | Insurance | Test Prep |

- Test Type: Angiogram
- Test Location: Barrett Center
- Other: test
- Ordered By: Ernst, Nicholas
- Ordering Dept: Management
- Ordering Facility: Anderson
- Requested By: Ernst, Nicholas
- Test Date: 10/11/2001
- Expected Results: 4/17/2002
- Arrival Time: 12:00:00 AM
- Test Time: 12:00:00 AM
- Contact Person: bill
- ☑ Patient has Port-A-Cath
- Diagnosis: test

[Close]

FIG. 28

INTERNET-BASED, CUSTOMIZABLE CLINICAL INFORMATION SYSTEM

CROSS REFERENCE TO RELATED APPLICATIONS

The present application claims the benefit of U.S. Provisional Application Ser. No. 60/378,245, filed May 7, 2002, the entire contents of which are incorporated herein by reference.

SUMMARY

The present invention is an Internet-based, or Web-based, customizable clinical (patients' records and care) information system ("CIS"). The invention includes software products that are customizable by the patient care facility (e.g., a hospital), and that reside on a central server that is accessible, via secure Internet connection, by those entering, accessing, modifying and/or approving the information stored therein. In the exemplary embodiment, each person accessing the CIS will log onto the CIS using a secret password or some other personal identification data and CIS will then provide a graphical user interface ("GUI"), specifically adapted to provide functionality specific to the needs/position of the user. For example, the GUI for a doctor may be different than a GUI for a pharmacist, which may be different than a GUI for a nurse, and so on. The functions and operations of each GUI may be customizable by a system administrator (who may also have his/her own GUI).

The CIS maintains databases of patient information that include the patient's permanent chart and certain "events" designated for or regarding the patient that may become additions to the patient's chart when approved by the patient's physician. Such "events" may include, for example, a patient's diagnosis, a prescription, a test result, a medication recording/transcription, etc. All events entered by user who is not the physician may be routed to the physician for approval by the physician using his/her GUI. The entry of events, routing of the events to the patient's physician, and the approval by the physician are all performed using the CIS of the present invention. Rules and tasks regarding these functions may be customizable by a system administrator.

Each GUI has icons for activating certain functional modules. The availability of such modules may depend upon the position/authority of the user. Such modules may include, without limitation:

Staging/Treatment Planning: The CIS may be set up with standardized rules for automatically generating patient treatment plans and/or disease staging to ensure continuity and consistency in patient care. Once a diagnosis has been made and approved, the CIS can be configured to automatically set up a treatment plan for the diagnosis. The CIS can also automatically schedule the treatments and services for the patient following that treatment plan, since it has access to the treatment facility schedules and medication inventories.

For diseases, such as cancer, requiring different treatments depending upon the "stage" of the disease, the module may provide a graphical form that allows the physician to define the precise stage that the disease presently has; and, once staged, the module may define the appropriate plan and make the appropriate treatment schedule for that patient.

Lab Test Tracking: Lab work and testing may be set up and reviewed using this module.

Weekend Care: Patient care over a particular weekend or standing orders applicable over a weekend may be set up and reviewed using this module.

Policies and Procedures: This module allows users to view and download applicable policies and procedures and also keeps a record of such access as evidence for regulatory purposes, for example.

Patients' Charts: This module provides many different ways to view patient chart information as well as many different ways to organize and provide access to the permanent charts.

The physicians GUI may have several different "in-boxes", into which are received "events" for the physician's approval. Such in-boxes may include internal prescriptions, pharmacy prescriptions, weekend care, documents, etc. It is possible that customization of the rules and actions for each of the in-boxes may be provided.

The pharmacy GUI is a specialized GUI that is essentially a separate module. It provides electronic record keeping for organizations that provide pharmacy services. It allows the pharmacy staff to electronically communicate with physicians for refills, confirmations and questions about unclear prescriptions. Users can access on-line patient records to view up-to-date medication histories, problem lists, treatment protocols, allergies and other clinical information. The module allows pharmacy technicians to fill prescriptions and allows the pharmacists to approve the prescriptions one at a time or on a batch approval basis.

The CIS may also keep a digital photograph of each patient within the database records for that patient. This digital photograph may then be printed onto any hard copies of the patient's chart and on any pharmaceutical labels for that patient. Therefore, this digital photograph may reduce any potential for mix-ups between the patients because it allows those administering the medications and treatments to match a digital photograph on the patient's chart or prescription label to the patient himself/herself.

The first exemplary embodiment utilizes Web-browsers on the various client (user) computers to access the Web-based CIS from the server(s). The second exemplary embodiment utilizes dedicated applications installed on the client (user) computers that communicate over the Internet (or some other network) to the central server(s) to access/modify the central databases and other centralized information.

Consequently it will be appreciated that certain aspects of the present invention include: a clinical information system that is Web/Internet based, whether it utilizes a browser-type user interface or a distributed application-type user interface; a clinical information system that includes automatic disease staging and associated treatment planning and/or scheduling; a clinical information system that tracks certain events/submissions and sorts such events/submissions into a physician's in-box for on-line approval by the physician, where such approval causes the event/submission to become an addendum to the patient's record; a clinical information system that is customizable by an administrator; a clinical information system that establishes, and makes available for on-line review and approval, patient care or standing orders over a weekend; a clinical information system that utilizes patients' photographs to ensure accurate identification and proper treatment; a clinical information system that creates and stores an audit trail record for all significant events.

More specifically, it is a first aspect of the present invention to provide a method for operating a computerized clinical information system for a healthcare facility that includes the steps of: (a) providing a clinical information system that includes a plurality of user computers operatively coupled to a global computer network (such as the Internet), and at least one computer server operatively coupled to the global computer network, where the computer server has access to at least one clinical information memory source, and is operative to communicate with the user computers and exchange clinical data between the clinical information memory source and the user computers over the global computer network in a secure manner, and where each of the user computers operate a software tool allowing a user to view and modify at least certain of the clinical data; (b) providing an electronic patient chart database on the clinical information memory source, where the electronic patient chart database has a plurality of patient chart records; (c) linking a patient chart record with a primary physician; (d) logging into the computerized clinical information system using the software tool on a first one of the user computers by a user other than the primary physician; (e) entering an event for submission to the patient chart record by the user using the software tool on the first one of the user computers; (f) logging into the computerized clinical information system using the software tool on a second one of the user computers by the primary physician linked with the patient chart record; (g) routing the event to the second one of the user computers for review and approval by the primary physician; (h) reviewing and approving the event by the primary physician using the software tool on the second one of the user computers; and (i) adding the approved event to the patient chart record. In a more detailed embodiment, the event is a transcribed document, a prescription, an order, a test result, and/or a diagnosis. In a further detailed embodiment the software tool on the second one of the user computers provides the primary physician with a graphical user interface that includes a graphical "in-box", and the method includes the step of displaying the event by the graphical user interface on the second one of the user computers in the graphical in-box for the reviewing and approving step. In a further detailed embodiment the displaying step includes the step of displaying a plurality of events in the graphical in-box. Alternatively, the graphical user interface on the second one of the user computers includes a plurality of in-boxes, each of which is reserved for a particular category of events, and the displaying step includes the step of displaying sub-sets of the plurality of events in the respective plurality of in-boxes depending upon categories of the respective plurality of sub-sets. The plurality of in-boxes may include a transcribed document in-box, a prescription in-box, and/or an order in-box; and may also include a test result in-box and/or a message in-box.

In an alternate detailed embodiment of the first aspect of the present invention, the event is a diagnosis and the method further includes the step of establishing a treatment program for the treatment of the diagnosed disease. In a further detailed embodiment, the step of establishing a treatment program further includes the step of establishing a treatment schedule for implementing the treatment program. In yet a further detailed embodiment, the clinical information memory source includes a plurality of use schedules for a corresponding plurality of the healthcare facility's resources, and the step of establishing the treatment schedule includes the steps of updating the use schedules to reserve the healthcare facility's resources in accordance with the treatment program. In yet a further detailed embodiment, the updating step includes the steps of checking the use schedules for openings and filling openings in the use schedules according to the treatment program; the method further includes the step of adding the treatment schedule to the patient chart record; and/or the step of establishing a treatment schedule includes the step of establishing a medication schedule. In an alternate further detailed embodiment, the step of establishing a treatment program for the treatment of the diagnosed disease includes the step of applying a set of expert rules against the diagnosed disease. In another alternate further detailed embodiment, the diagnosed disease includes a stage of the diagnosed disease and the method further comprises the steps of providing a disease staging software tool on one of the user computers, where the disease staging software tool includes a plurality of condition fields pertaining to diagnosed or recorded conditions of a patient and includes a set of expert rules for determining a stage of the disease based upon the diagnosed or recorded conditions of the patient; completing the condition fields on the disease staging software tool by a user on the one of the user computers; and processing the completed condition fields against the set of expert rules to determine the stage of the disease.

In another alternate detailed embodiment of the first aspect of the present invention information pertaining to the routing, reviewing and approving steps are recorded in a central audit database. And in another alternate detailed embodiment of the first aspect of the present invention, the reviewing and approving steps include the step of modifying the event by the primary physician. In a further detailed embodiment, versions of the event existing before and after the modifying step are stored in a central audit database.

It is a second aspect of the present invention to provide a method for operating a computerized clinical information system for a healthcare facility that includes the steps of: (a) providing a clinical information system that includes a plurality of user computers operatively coupled to a global computer network (such as the Internet), and at least one computer server operatively coupled to the global computer network, where the computer server has access to at least one clinical information memory source, and operative to communicate with the user computers and exchange clinical data between the clinical information memory source and the user computers over the global computer network in a secure manner, and where each of the user computers operating a software tool allowing a user to view and modify at least certain of the clinical data; (b) providing an electronic patient chart database on the clinical information memory source, where the electronic patient chart database has a plurality of patient chart records; (c) logging into the computerized clinical information system using the software tool on a first one of the user computers by a user; (d) diagnosing a stage of a patient's disease, where the patient has a chart record in the electronic patient chart database; and (e) adding the diagnosed disease stage to the patient's chart record. In a further detailed embodiment, the diagnosing step (d) further includes the steps of: (d1) providing a disease staging graphical user interface by the software tool, where the graphical user interface includes a plurality of condition fields pertaining to diagnosed or recorded conditions of a patient, and where the software tool includes a first set of expert rules for determining a stage of the disease based upon, at least in part, the diagnosed or recorded conditions of the patient entered into the graphical user interface; (d2) entering information pertaining to the patient's diagnosed or recorded conditions into the condition fields on the graphical user interface by a user on the one of the user computers; and (d3) processing the completed condition fields against the first set of expert rules to determine the stage of the disease. In yet a further detailed embodiment, the method further includes the step of (f) establishing a treatment program for the treatment of the diagnosed disease stage. In yet a further detailed embodiment, the step of establishing a treatment program (f) further includes the step of (f1) establishing a treatment schedule for implementing the treatment program. In yet a further detailed embodiment, the clinical information memory source includes a plurality of use schedules for a corresponding plurality of the healthcare facility's resources, and the step of establishing the treatment schedule (f1) includes the steps of updating the use schedules to reserve the healthcare facility's resources in accordance with the treatment program. In yet a further detailed embodiment, the updating step includes the steps of checking the use schedules for openings and filling openings in the use schedules according to the treatment program. In yet a further detailed embodiment the method further includes the step of adding the treatment schedule to the patient's chart record; and/or the step of establishing a treatment schedule includes the step of establishing a medication schedule.

It is a third aspect of the present invention to provide a method for operating a computerized clinical information system for a healthcare facility that includes the steps of: (a) providing a clinical information system that includes a plurality of user computers operatively coupled to a global computer network (such as the Internet), and at least one computer server operatively coupled to the global computer network, where the computer server has access to at least one clinical information memory source, and operative to communicate with the user computers and exchange clinical data between the clinical information memory source and the user computers over the global computer network in a secure manner, and where each of the user computers operating a software tool allowing a user to view and modify at least certain of the clinical data; (b) providing an electronic patient chart database on the clinical information memory source, where the electronic patient chart database has a plurality of patient chart records; and (c) for each of the patient chart records, storing a digital image of the patient associated with the respective patient chart record. In a further detailed embodiment, the method further includes the step of (d) printing a tangible copy of a portion of the patient chart record, where the tangible copy includes a printed version of the digital image of patient stored in the patient chart record. In yet a further detailed embodiment, the tangible copy includes a prescription label; the tangible copy includes an order; and/or the tangible copy includes at least a portion of a treatment schedule.

It is a fourth aspect of the present invention to provide a method for operating a computerized clinical information system for a healthcare facility that includes the steps of: (a) providing a clinical information system that includes a plurality of user computers operatively coupled to a global computer network (such as the Internet), and at least one computer server operatively coupled to the global computer network, where the computer server has access to at least one clinical information memory source, and operative to communicate with the user computers and exchange clinical data between the clinical information memory source and the user computers over the global computer network in a secure manner, and where each of the user computers operating a software tool allowing a user to view and modify at least certain of the clinical data; (b) providing an electronic patient chart database on the clinical information memory source, where the electronic patient chart database has a plurality of patient chart records; (c) linking a patient chart record with a primary physician; (d) logging into the computerized clinical information system using the software tool on a first one of the user computers by a user that is a pharmacist, a pharmacy technician, a nurse, a non-primary physician or a pharmacy assistant; (e) entering at least one request that is a new prescription, a prescription renewal, a treatment, a test or an order for approval by the primary physician by the user using the software tool on the first one of the user computers; (f) logging into the computerized clinical information system using the software tool on a second one of the user computers by the primary physician; (g) routing the request to the second one of the user computers for review and approval by the primary physician; (h) reviewing and approving the request by the primary physician using the software tool on the second one of the user computers; and (i) adding the approved request to the patient chart record. In a further detailed embodiment the method further includes the step of notice of approval of the request back to the user logged onto the computerized clinical information system. In yet a further detailed embodiment the patient chart record includes a digital image of the patient and the method further includes the step of printing a tangible copy of a portion of the patient chart record, where the tangible copy includes a printed version of the digital image of patient stored in the patient chart record. In yet a further detailed embodiment the tangible copy includes a prescription label, the tangible copy includes an order, and/or the tangible copy includes at least a portion of a treatment schedule.

In an alternate detailed embodiment of the fourth aspect of the present invention, the software tool on the first one of the user computers provides a first graphical user interface customized for use by the user; and the software tool on the second one of the user computers provides a second graphical user interface customized for use by the primary physician. In a further detailed embodiment, each of the first and second graphical user interfaces provide access to the patient chart record. In yet a further detailed embodiment, the first and second graphical user interfaces provide access to one or more of the following functions: drug-drug interaction checking; drug-disease interaction checking; drug warnings; drug pharmacology; pregnancy and lactation hazard information; therapeutic duplication checking; and drug-allergy checking.

In another alternate detailed embodiment of the fourth aspect of the present invention, the request is a request for weekend care. In a further detailed embodiment, the second one of the user computers is a computer remote from the healthcare facility. In yet a further detailed embodiment, the second one of the user computers is a hand-held computer.

In yet another alternate detailed embodiment of the fourth aspect of the present invention, the request is of a new prescription and/or an order, and the method further includes the step of, prior to the routing step, automatically checking a requested dosage of the new prescription or order against safety guidelines. In a further detailed embodiment, the step of automatically checking a requested dosage of the new prescription and/or order against safety guidelines includes the step of providing a minimum and maximum dosage for at least one of a patient's body weight and a patient's condition.

It is a fifth aspect of the present invention to provide a method for operating a computerized clinical information system for a healthcare facility that includes the steps of: (a) providing a clinical information system that includes a plurality of user computers operatively coupled to a global computer network (such as the Internet), and at least one computer server operatively coupled to the global computer network, where the computer server has access to at least one clinical information memory source, and operative to communicate with the user computers and exchange clinical data between the clinical information memory source and the user computers over the global computer network in a secure manner, and where each of the user computers operating a software tool allowing a user to view and modify at least certain of the clinical data; (b) logging into the computerized clinical information system using the software tool on a first one of the user computers by an administrator; and (c) modifying the set of rules by the administrator to customize the operations of the clinical information system.

BRIEF DESCRIPTION OF THE DRAWINGS

FIG. 6 illustrates an example of a view-medication dialog interface according to an exemplary embodiment of the present invention;

FIG. 7 illustrates an example of an order in-box screen of a physician's graphical-user-interface according to an exemplary embodiment of the present invention;

FIG. 9 illustrates an example of a batch-submit-dictations screen of a physician's graphical-user-interface according to an exemplary embodiment of the present invention;

FIG. 19 provides an example drug-interaction screen according to an exemplary embodiment of the present invention;

FIG. 21 provides an example form interface for staging breast cancer diagnosis and treatment according to an exemplary embodiment of the present invention;

FIG. 28 is an example view-test interface according to a distributed-application embodiment of the present invention.

DETAILED DESCRIPTION

The present invention is an Internet-based, or Web-based, customizable clinical (patients' records and care) information system ("CIS"). The invention includes software products that are customizable by the patient care facility (e.g., a hospital), and that reside on a central server that is accessible, via secure Internet connection, by those entering, accessing, modifying and/or approving the information stored therein. In the exemplary embodiment, each person accessing the CIS will log onto the CIS using a secret password or some other personal identification data and CIS will then provide a graphical user interface ("GUI"), specifically adapted to provide functionality specific to the needs/position of the user. For example, the GUI for a doctor may be different than a GUI for a pharmacist, which may be different than a GUI for a nurse, and so on. The functions and operations of each GUI may be customizable by a system administrator (who may also have his/her own GUI).

The CIS maintains databases of patient information that include the patient's permanent chart and certain "events" designated for or regarding the patient that may become additions to the patient's chart when approved by the patient's physician. Such "events" may include, for example, a patient's diagnosis, a prescription, a test result, a medication recording/transcription, etc. All events entered by user who is not the physician may be routed to the physician for approval by the physician using his/her GUI. The entry of events, routing of the events to the patient's physician, and the approval by the physician are all performed using the CIS of the present invention. Rules and tasks regarding these functions may be customizable by a system administrator.

Figure 1:
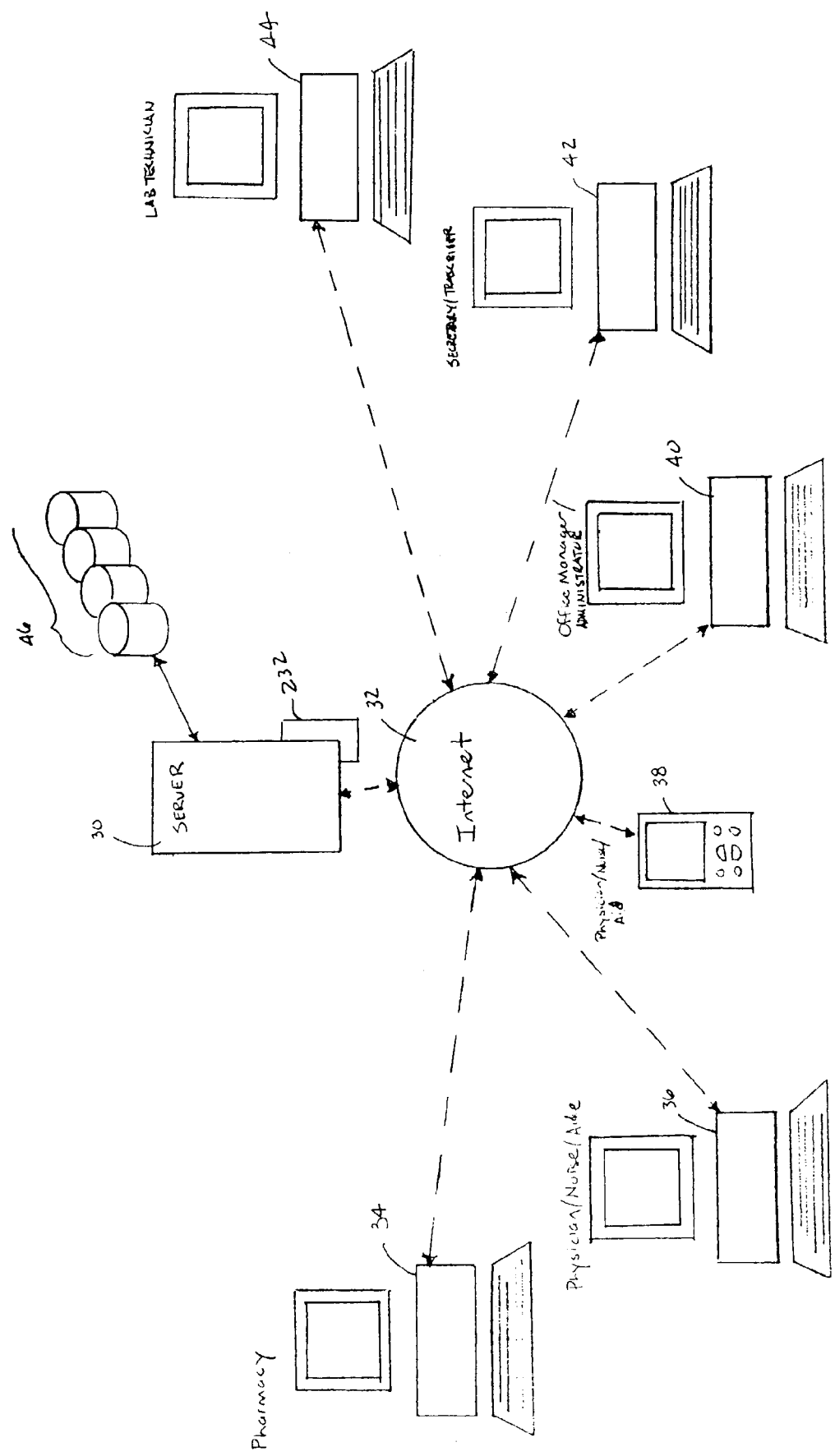
FIG. 1 illustrates a block diagram representation of an exemplary system configuration for the present invention.

As shown in FIG. 1, in an exemplary embodiment, the CIS software resides on a computer server 30 (or on group of servers as desired) operatively coupled to a computer network such as the Internet 32. The system also includes a plurality of user computers associated with a patient care facility, such as a hospital, where such user computers are operatively coupled to the Internet 32 and are, thereby, accessible to the CIS resident on the server 30. The user computers may include a pharmacy computer 34 accessible to pharmacists and/or technicians within the facility's pharmacy; a physician/nurse/aide computer 36 accessible to a physician/nurse/aide in the hospital or at a remote location; a physician/nurse/aide handheld computer 38, again accessible to a physician/nurse/aide within the care facility or at a remote location; an office manager/administrator computer 40; a secretary/transcriber computer 42; and a lab technician computer 44. In addition to the CIS system operating on the server, the CIS system will have access to various databases 46 which include, without limitation: patient information and charts databases, testing schedule databases, various event databases, audit trail databases, etc.

In the first exemplary embodiment, the system is generally configured to operate as follows: a user at one of the user computers, such as the physician/nurse/aide computer 36, will access the Internet 32 using the computer 36 and then contact the CIS operating on the server 30 by addressing or linking to a CIS website generated by the server 30 using any manner of Internet communication and data transfer protocol as is, or will be known to those of ordinary skill in the art. Upon establishing a communication link with the server 30, the server will then download necessary code over the Internet 30 to the user computer 36, which will then be interpreted by an interpreter program operating on the user's computer 36 (such as a Web browser) and be displayed on the user's computer as directed by the code downloaded from the server 30. Preferably, prior to accessing critical information provided by the CIS, the user at the particular computer will first need to log on to the CIS system using any known security log-on procedure as available to those of ordinary skill in the art; such as, for example, requiring the user to submit a user-name and password that is transmitted over the Internet to the server and verified by the server. Additionally, the communications between the various client computers and the server computer are encrypted for security purposes using a standard encryption protocol (2048 bit encryption in the exemplary embodiment).

Advantageously, the Web based CIS allows users to access the CIS over any computer/device operatively coupled to the Internet. Therefore, it is possible for physicians to access the CIS at his or her home or at remote locations within the patient care facility or outside of the patient care facility.

While the first exemplary embodiment utilizes Web-browsers on the various client (user) computers 34-44 to access the Web-based CIS from the server(s) 30, a second exemplary embodiment utilizes dedicated applications installed on the client (user) computers 34-44 that communicate over the Internet (or some other network) 32 to the central server(s) 30 to access/modify the central databases 46 and other centralized information. In the second exemplary embodiment, a distributed application is installed onto the various client (user) computers 34-44, which provides the various functionalities described herein with the first exemplary embodiment, and utilizes Microsoft's .NET Web services platform, for example, to access and/or modify the centralized databases 46 and other centralized information from the server(s) 30.

The exemplary embodiments of the present invention provide customized graphical user interfaces for a plurality of different purposes/users that will be accessing the CIS. These graphical user interfaces may hereinafter be referred to as "digital-dashboards" or "dashboards." As mentioned, each dashboard may be customized for each individual's role with the patient care facility. For example, there could be a customized physician's dashboard, a customized medical assistant's dashboard, an office manager dashboard, a pharmacy dashboard, etc.

Figure 2:
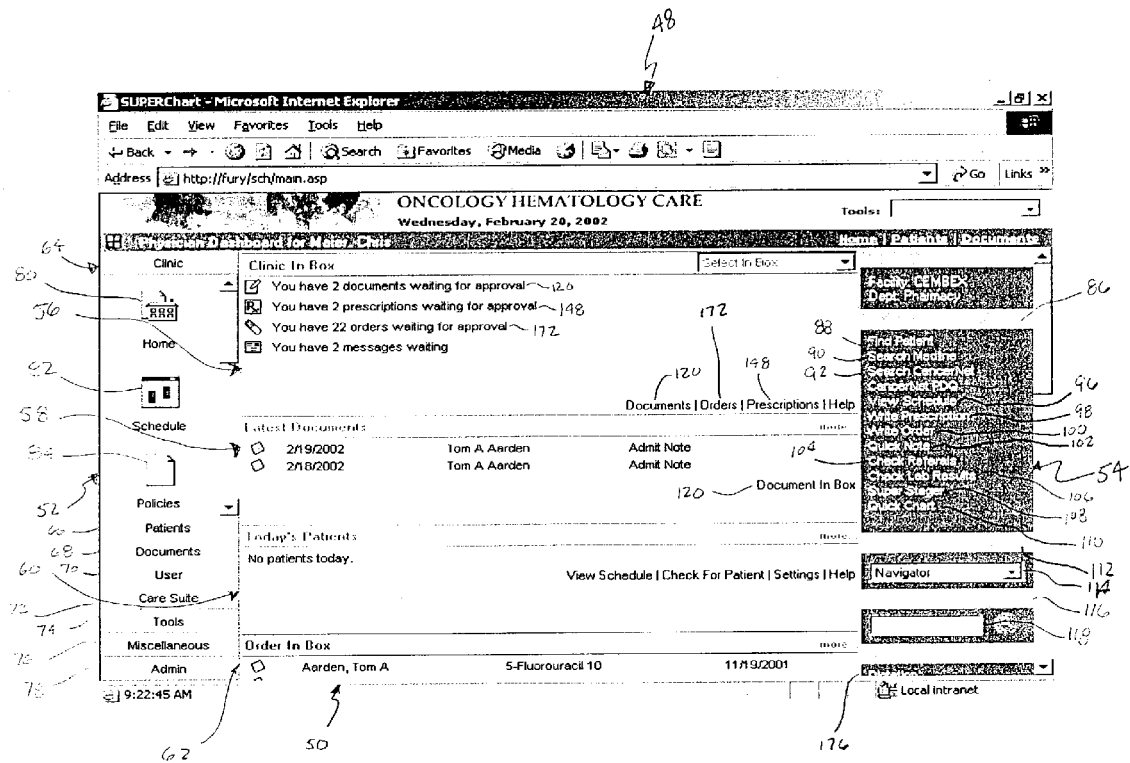
FIG. 2 illustrates an example of a physician's graphical-user-interface or "digital-dashboard" 48 according to an exemplary embodiment of the present invention.

As shown in FIG. 2, physician's digital-dashboard 48 includes three windows: a primary window 50, a function-select window 52 and a tools-select window 54. The primary window 50 provides representations of available "in-boxes" and other related boxes, each of which lists items for review and/or disposition by the physician. For example, a "Clinic In-Box" 56 is provided that informs the physician of the number of documents waiting for approval, the number of prescriptions waiting for approval, the number of orders waiting for approval and the number of messages waiting for the physician. The present example of the physician's dashboard 48 also includes a "Latest Documents Box" 58 that presently lists the two documents waiting for the physician's review and approval. The "Today's Patients Box" 60 provides a schedule of patients scheduled to be seen for a given day by the physician. The "Order In-Box" 62 provides a list of the pending orders that are waiting for the physician's approval.

The function-select window 52 provides a plurality of functions provided by the CIS and available to the physician, where each of the functions are categorized and accessible via menu bars such as the "Clinic" menu bar 64, the "Patients" menu bar 66, the "Documents" menu bar 68, the "User" menu bar 70, the "Care Suite" menu bar 72, the "Tools" menu bar 74, the "Miscellaneous" menu bar 76 and the "Admin" menu bar 78. Under the selected "Clinic" menu bar 64 three icons are provided corresponding to three functions selectable by the physician. The first function icon, "Home" 80, will take the physician to the home page of the physician dashboard, the second icon, "Schedule" 82, will take the physician to the physician's schedule/calendar page and the third icon, "Policies" 84, will take the physician to the policies page. It will be apparent to those of ordinary skill in the art that when the CIS, a digital dashboard or a particular screen, window, icon or link is described herein "taking" the user to another screen or to another function, that this operation may involve a hyperlink type operation whereupon activation of a particular link or icon will cause the browser program running on the user's computer to contact the server 30 over the Internet requesting the server 30 to transmit code for the particular page, frame or function that has been requested. Graphical-user-interface operations and options of such hyperlinking, icon activations and function requests are widely known and diverse, and are available to those of ordinary skill in the art.

The tools window 54 provides a number of tools available to the physician. Such tools include a plurality of icons or hyperlinks under the "Tasks" menu bar 86 that will take the user to a window or page for performing the specific task listed by the icon/hyperlink. For example, the various tools listed under the "Tasks" menu bar include a "Find Patient" tool 88, a "Search Medline" tool 90 that will provide a search engine for searching the Medline database, a "Search CancerNet" tool 92 that will allow the physician to search the CancerNet database, a "CancerNet PDQ" tool 94, a "View Schedule" tool 96, a "Write Prescription" tool 98, a "Write Order" tool 100, a "Quick Note" tool 102, a "Check Referrals" tool 104, a "Check Lab Results" tool 106, a "Superstager" tool 108 and a "Quick Chart" tool 110. Most of the tools mentioned above are self explanatory and some of these tools will be described in greater detail below. A "Go To" menu bar 112 provides a pull down menu 114 that allows the physician to quickly access a particular page or file available on the dashboard to the physician. A "Find Patient" menu bar 116 provides a field 118 into which the physician can enter a patient's name or a portion of a patient's name and a search utility operating on the CIS will search the patient information database in the group of databases 46 for a patient matching the search query provided in the box 118.

Figure 3:
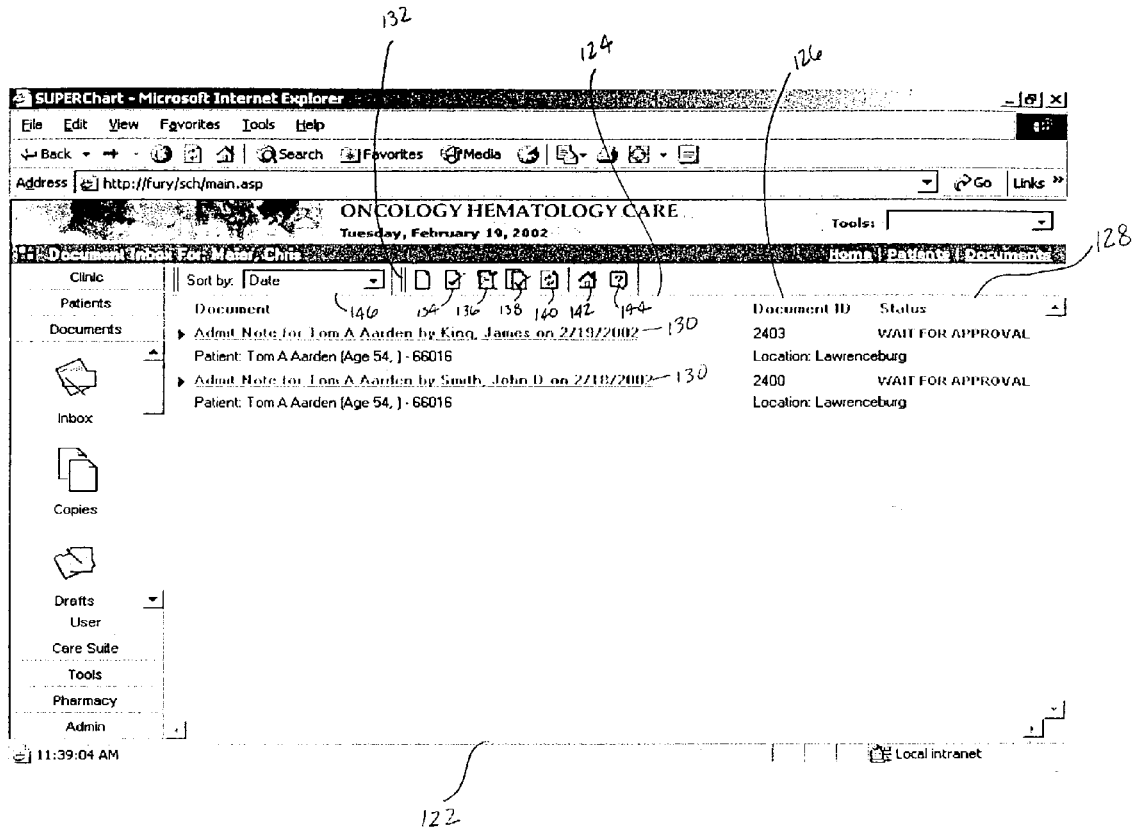
FIG. 3 illustrates an example of a document in-box screen of a physician's graphical-user-interface according to an exemplary embodiment of the present invention.

If, in the primary window 50, the physician activates any of the available "Documents" icons or hyperlinks 120, the CIS will take the physician to the documents "In-Box" 122 as shown in FIG. 3.

Figure 4:
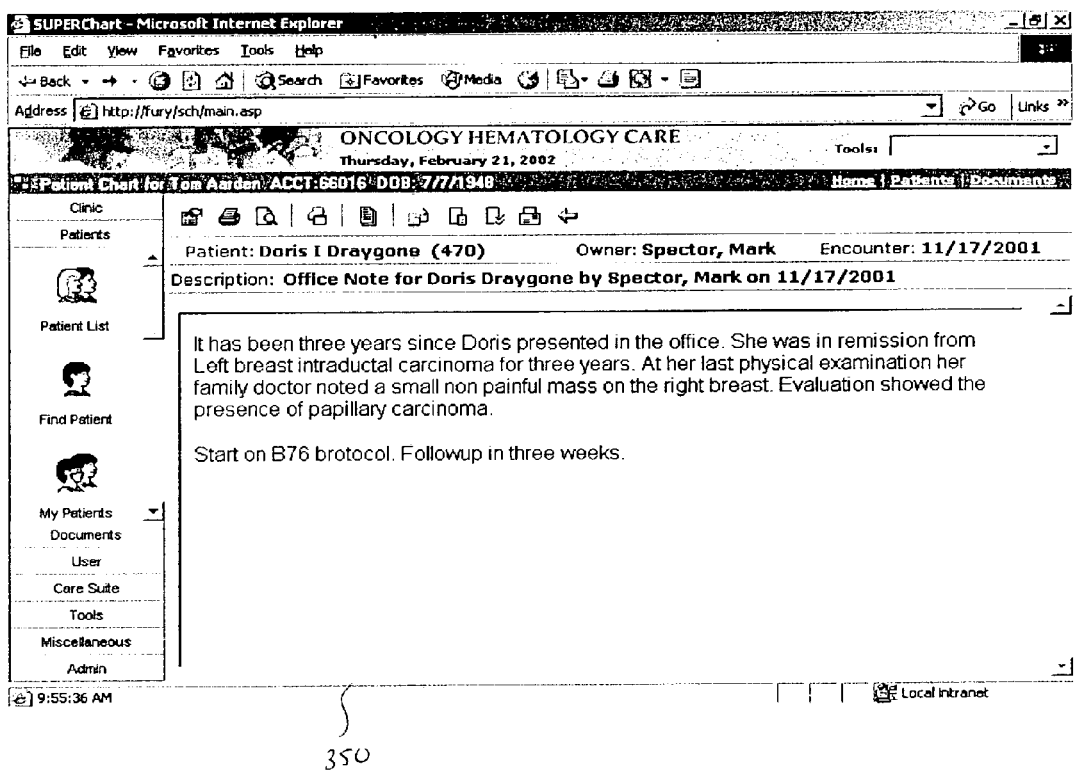
FIG. 4 illustrates an example of a document review/revise screen of a graphical-user-interface according to an exemplary embodiment of the present invention.

As shown in FIG. 3, the document in-box screen 122 lists the various documents (transcribed dictations, admission notes, etc.) waiting for review and approval by the physician. Each document is listed by the name of the document, who it was prepared by, the date it was prepared, and for what patient it was prepared for under the "Document" column 124; a document ID under the "Document ID" column 126; and the status of the document under the "Status" column 128. The name of the document 130 as provided in the "Document" column 124 is an icon/hyperlink to a page (see FIG. 4) that will bring up the document (taken from one of the databases 46) in a word processor type screen 350 for the physician's review and allow the physician to make changes or additions to the document. In addition, this screen 350 also provides the physician with the ability to rout the document to others for their consideration or approval. By "right-clicking" on a particular entry, the physician is provided with a menu that allows the physician to view the document, print the document and/or fax the document.

A menu bar 132 in the document in-box screen 122 provides a number of icons that allow the physician to approve a document 134, reject a document 136, approve multiple documents 138, refresh the page 140, return to the home page 142, and ask for help 144. The menu bar 132 also provides a pull-down menu 146 that allows the physician to sort the documents in a plurality of selectable manners.

Upon approving a particular document, by activating the approve-a-document icon 134, for example, the CIS will then store the approved document as part of the patient's chart for which the document was created. As discussed above, the physician has the opportunity to make changes or additions to the documents. For tracking and security purposes, the CIS saves in one of the databases 46 every version of the documents, along with the date the version was created and the person who created the particular version. Along with the standard encryption securities suggested above, the CIS creates digital signatures that are attached to each document created or modified. These digital signatures are message digests or "hash". For example, a document's digest is reviewable to guarantee the author and revision data.

The document module supports several different kinds of notes in addition to the word processor note. For example, it is possible for the user to scan in information where the scanned information can be translated into text that is placed in one of the documents. The documents can be routed for approval by physicians (see FIG. 2) and an audit trail will be kept of all such routing information. It is also possible to download documents from external sources and incorporate the documents into the CIS.

Figure 5:
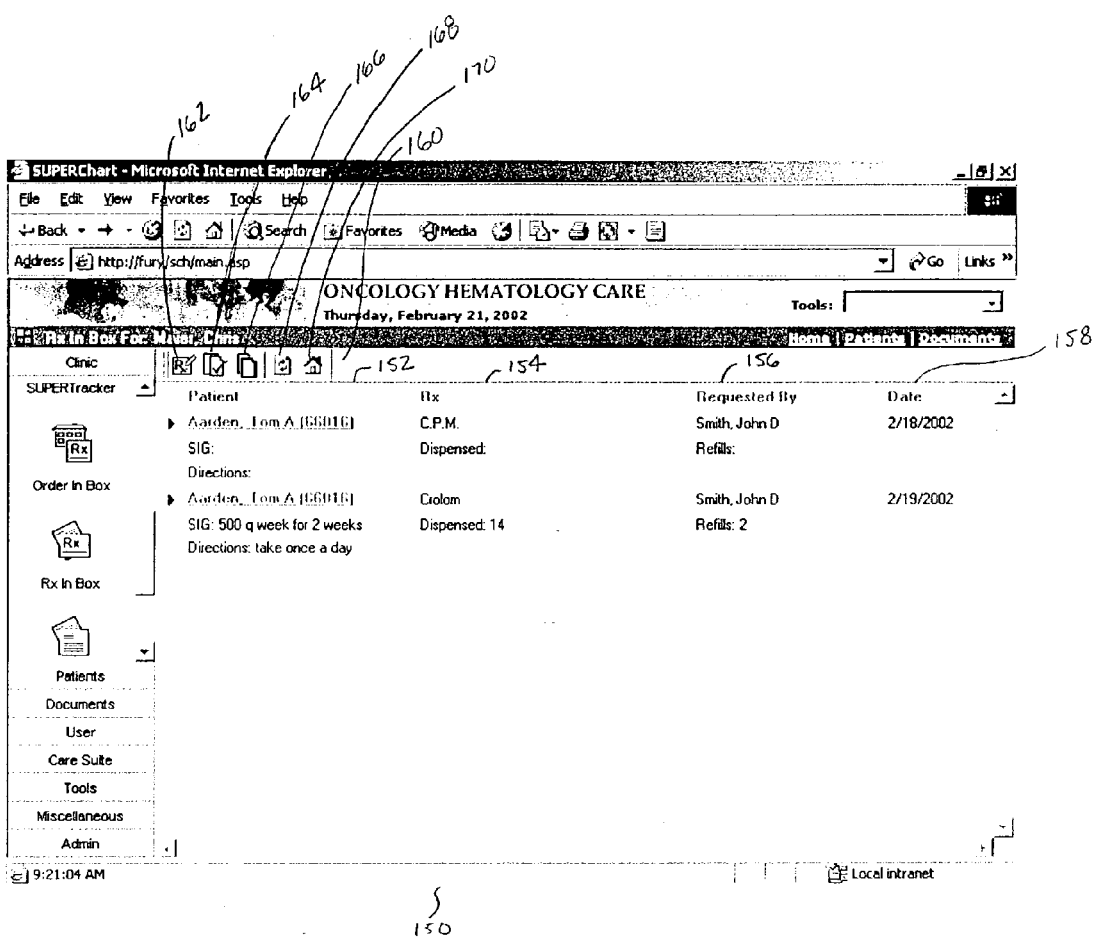
FIG. 5 illustrates an example of a prescription in-box screen of a physician's graphical-user-interface according to an exemplary embodiment of the present invention.

Referring back to FIG. 2, if the physician activates the hyperlink/icon 148 associated with the prescriptions waiting for approval, the CIS will take the physician to the prescription in-box screen 150 as shown in FIG. 5.

Referring to FIG. 5, the prescription in-box screen 150 lists the various prescriptions waiting for approval by the physician. In this exemplary embodiment, the prescriptions are identified in four columns: a "Patient" column 152 identifying the name of the patient for which the prescription is requested, the dosage ordered and the directions; a "RX" column 154 identifying the prescription that is being requested; a "Requested By" column 156 identifying the pharmacist, nurse or physician requesting the pharmaceutical; and a "Date" column 158 indicating the date of such request. The prescription in-box screen 150 also provides a menu bar 160 with a plurality of icons that include an "Rx" icon 162, an icon 164 which allows the physician to approve the requested pharmaceutical for the selected patient, an icon 166, a refresh icon 168 for allowing the physician to refresh the prescription in-box screen and a home page icon 170 allowing the physician to request to be taken back to the home page of the physician's dashboard.

Upon approving a particular pharmaceutical, by activating the approve a document icon 164, for example, the CIS will then store the approved pharmaceutical as part of the patient's chart for which the document was created and the CIS will also notify the pharmacy that the pharmaceutical is approved for administering to the patient or for filling.

If the physician "right-clicks" on a particular entry in the prescription in-box screen 150, a menu will be provided that allows the physician to view the medication, request a refill of the medication, remove the medication, print the medication, view information on the medication and/or fax a prescription for the medication (to a pharmacy, for example). FIG. 6, show an example "view medication" window 171.

Referring back to FIG. 2, if the physician activates one of the icons or hyperlinks 172 pertaining to the orders waiting for approval, the CIS will take the physician to the order inbox screen 174 as shown in FIG. 7. The order in-box screen operates much in the same way as the prescription in-box screen as shown in FIG. 5. The primary difference between the prescriptions and the orders are that prescriptions are generated by the pharmacy of the care facility while the orders are generated internally within the care facility (such as in the patient's rooms themselves, for example).

Figure 8:
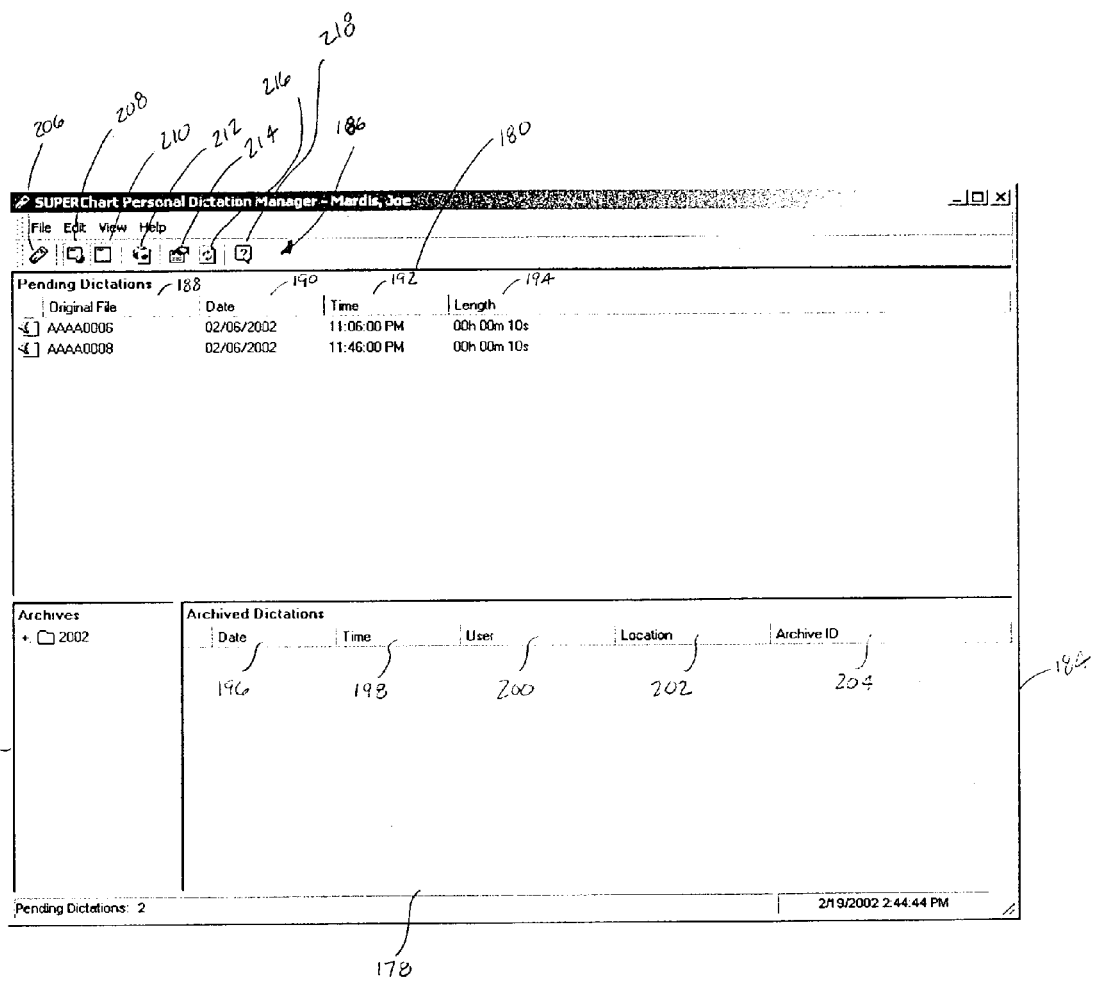
FIG. 8 illustrates an example of a personal dictation manager screen of a physician's graphical-user-interface according to an exemplary embodiment of the present invention.

Referring back to FIG. 2, the tools window 54 also provides a dictation manager tool 176 that, when activated, will take the physician to the personal dictation manager screen 178 as shown in FIG. 8. The personal dictation manager is used to manage digital dictation files produced by digital recorders, personal digital assistants, and digital recording software accessible by the physician. The personal dictation manager automatically retrieves digital dictation audio files from a digital recorder (which may be operatively coupled to the physician's computer 36/38) and then uploads the files to a centralized location, such as a database 46 accessible by the server 30, for pickup by the transcription staff using the transcriber computer 42 operatively coupled to the Internet 32 (see FIG. 1). The personal dictation manger logs all file transfer activity in a database log 46 and automatically archives the digital dictation files in a database 46 for safekeeping.

As shown in FIG. 8, the personal dictation manger screen 178 includes three windows: a "Pending Dictations" window 180, which displays a list of pending dictations; an "Archives" window 182, which displays a list of archive directories; and an "Archive Dictations" window 184 which displays the archived dictations for the selective archives files in the archive window 182. The personal dictation manger screen also includes a main tool bar/menu bar 186 where the primary functions of the personal dictation manger may be accessed and activated. The pending dictation list window 180 displays dictations that have been downloaded from a dictation device (like a digital recorder) or imported into the system from sound recording programs. The Pending Dictation window 180 includes an "Original File" column displaying the original file name for each dictation, a "Date" column 190 illustrating the date that the dictation was created, a "Time" column 192 illustrating the time that the dictation was created and a "Length" column 194 indicating the length of the dictation.

The personal dictation manager window is configured such that if the user "right-clicks" on one of the pending dictations in the pending dictation list a pop-up menu will be displayed that allows the user to, for example: play the particular dictation, submit the particular dictation to the CIS for transcription, delete the particular dictation or refresh the screen. The "Archives" window 182 shows a list of dated folders that contain archived dictation files. Selecting one of the directories in the window 182 causes dictations for that date to be displayed in the "Archived Dictations" window 178. The archived dictation list includes a "Date" column 196 showing the date that the particular archived dictation was recorded, a "Time" column 198 showing the time that the particular archived dictation was recorded, a "User" column 200 indicating the user ID for the recording, a "Location" column 202 indicating the location of the recording and an "Archive ID" column 204 indicating the identification number for the archived dictation.

If the user "right-clicks" on one of the archived dictations in the archived dictation list provided in the "Archived Dictations" window 178, a pop-up menu is displayed that allows the user to, for example: play the dictation, export the dictation, re-submit the dictation, delete the dictation, view the properties of the dictation, e-mail the dictation, or refresh the screen. The tool bar 186 includes an icon 206 that allows the user to connect to the electronic dictation device, an icon 208 that allows the user to hide/show the pending dictation list, an icon 210 that allows the user to hide/show the archived dictation list, an icon 212 that allows the user to submit all dictations, an icon 214 that allows the user to adjust the settings of the personal dictation manager, a "refresh" icon 216 and a "help/about" icon 218.

Upon activating the "connect to dictation device" icon 206, the system will retrieve digital recording files from the user's computer that were recorded using a digital recording device operatively coupled to the user's computer and will download the selected files to the CIS over the Internet to be stored in one of the databases 46 associated with the physician and/or associated with digital transcriptions. Once downloaded, the downloaded file will thereafter appear in the "Pending Dictations" window 180. When the "submit all dictations" icon 212 is activated by the user, a batch submission screen will be generated as shown in FIG. 9.

The batch submission screen 220 shown in FIG. 9 includes a field 22 for the user to enter his/her user name, a field 224 for the user to enter his/her location, and fields 226, 228 that allows the user to select beginning and end dates for the range covered by the dictations that the user is submitting. The user will then activate the "Submit" button 230 and the dictation files will be processed as follows: the dictation files will be converted to a format that can be read by the transcription department's software; the dictation files are transmitted to an FTP server 232 (see FIG. 1); and the dictation files are archived in one of the accessible databases or archives 46. At this point, the dictation files will be moved from the pending dictations list in the Pending Dictations window 180 of FIG. 8 to the archived dictations list in the Archived Dictations window 182. The system also provides capabilities for submitting a single dictation at a time, for sending a dictation to a transcriber via e-mail, for exporting a dictation from a drive of the user's computer or from another computer or system over a network or Internet operatively coupled to the computer for importing a dictation file, etc.

Once on the FTP server 232, the transcription department may be notified of available dictations and will access the digital recordings using their customized dashboards accessing the CIS from their respective computers 42. The transcribers will download the digital recordings from the FTP server 232 onto their respective computers 42, play the recordings using their computers 42, and transcribe the recordings using a word-processor on the computer. Once transcribed, the documents will be uploaded back to the CIS and stored in an associated one of the databases 46, and the physician will be notified of a pending document waiting for approval as discussed above.

The CIS of the present invention also provides a pending transactions module that allows a system administrator, at computer 40 for example, to view any transcriptions that failed to be incorporated directly into the system (i.e., failed to be routed to the correct physician, for example), correct the routing information and re-rout the transcription to the proper in-box for approval. The module does not allow the administrator to change any of the transcribed data (i.e., text), just the identification and/or routing data.

Figure 10:
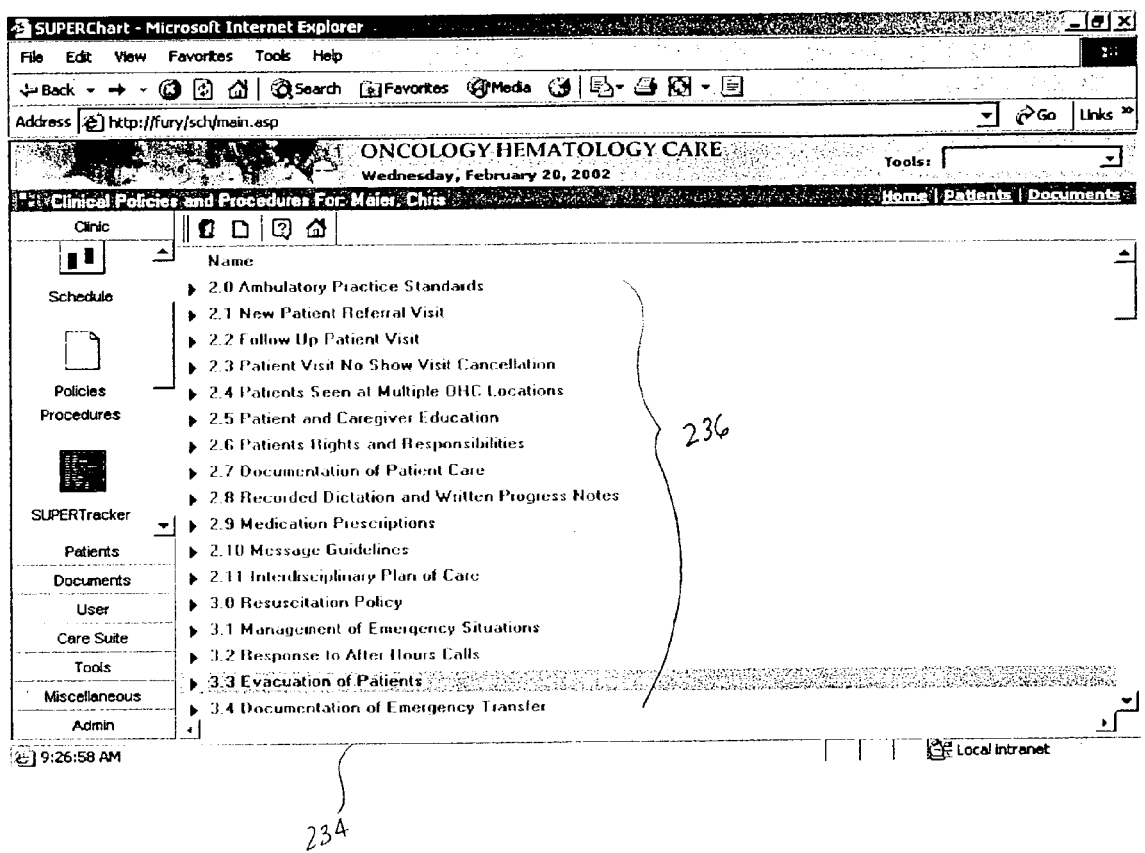
FIG. 10 illustrates an example of a policies-and-procedures select-for-review screen of a physician's graphical-user-interface according to an exemplary embodiment of the present invention.

Referring back to FIG. 2, upon activation of the policies icon 84 on the physician's digital dashboard, a policies and procedures screen 234 will be presented as shown in FIG. 10, which provides a selection of icons/hyperlinks 236, each of which will cause a selected policy and/or procedure to be displayed on the user's computer screen. In the exemplary embodiment, the CIS will keep track of all of the policies and procedures reviewed by each particular user and store such data in one of the databases 46. Such information can be useful for accreditation purposes, for example.

Figure 11:
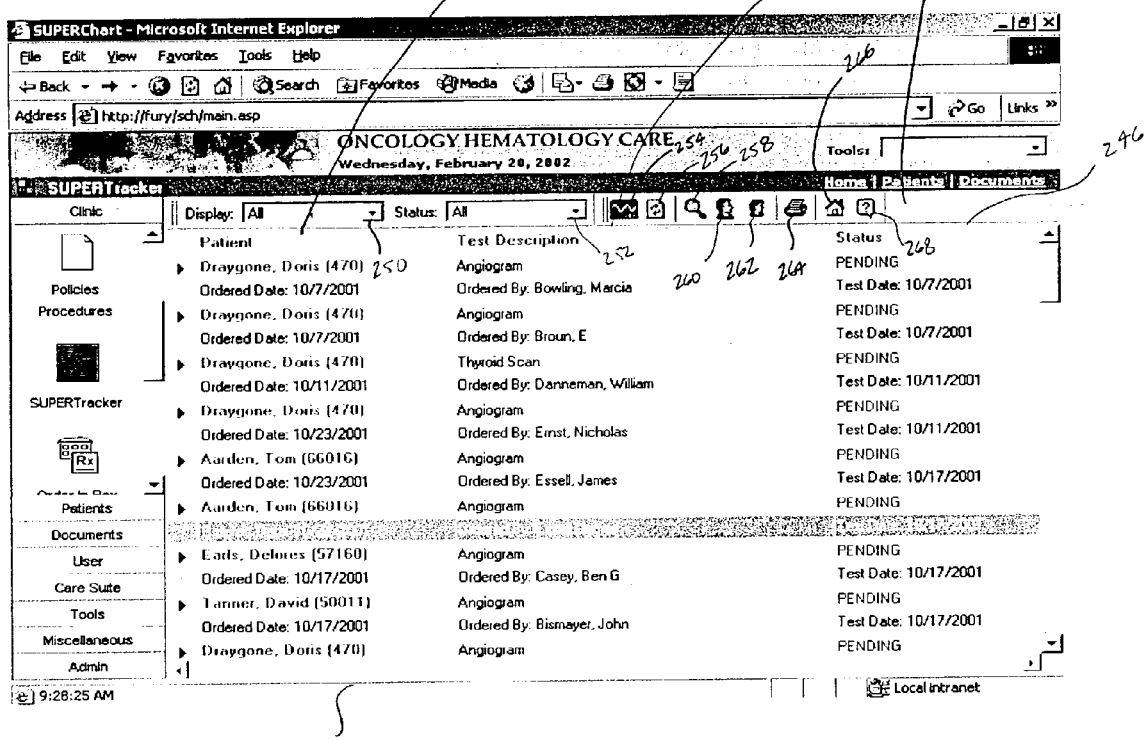
FIG. 11 illustrates an example of a lab technician's graphical-user-interface screen for organizing and tracking the administration and scheduling of patients' lab tests and procedures.
Figure 12:
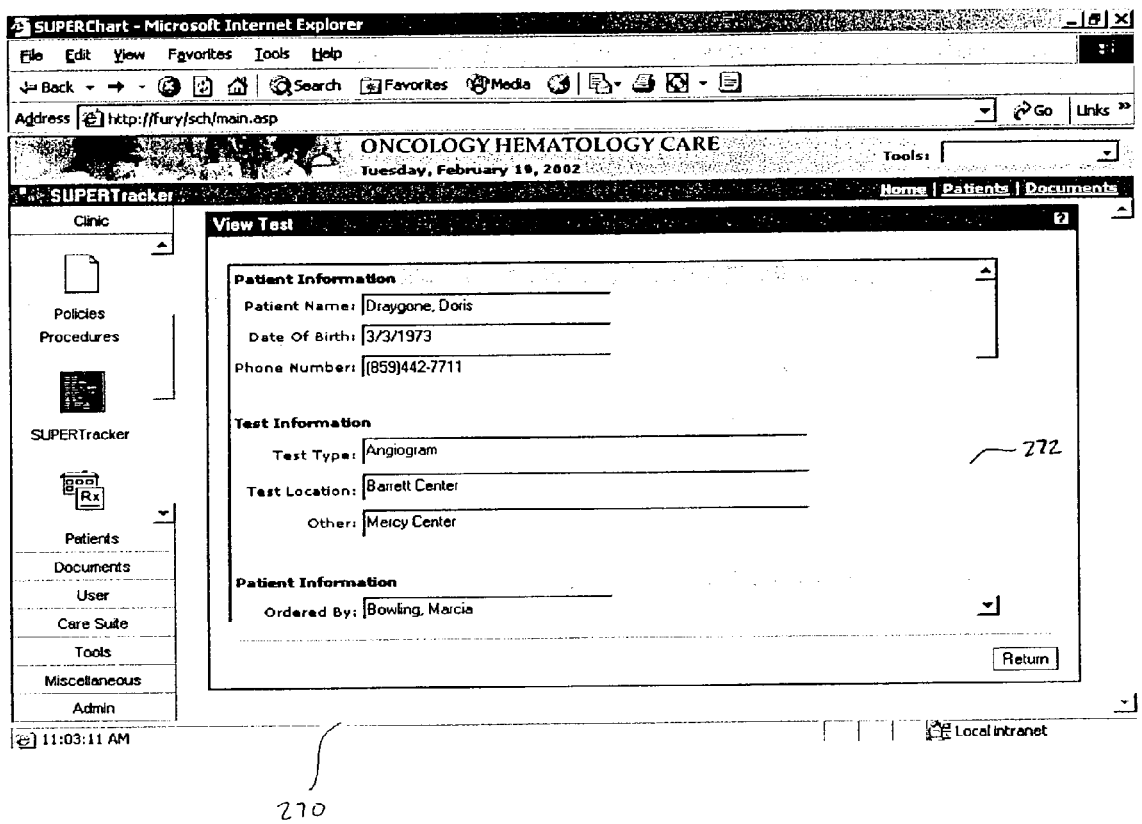
FIG. 12 illustrates an example of a lab technician's view-test graphical-user-interface screen.

FIG. 11 provides an example dashboard 240 which may be used, for example by lab technicians for organizing and tracking the administration and scheduling of patients' lab tests and procedures. This dashboard allows the lab technicians to schedule tests for patients and review the status of such tests (i.e., if and when the tests have been performed). The dashboard 240 has a main window that includes a "Patient" column 242 that lists the name of the patient ordered for a particular test and the date that the test was ordered, a "Test Description" column listing a short description of the test ordered and the technician or doctor ordering the test and a "Status" column 246 listing the status of the test along with the date that the test was scheduled. A menu bar 248 includes a "Display" pull down menu 250 that allows the user to select and order which tests are to be displayed in the window and also includes a "Status" pull down menu 252 which allows the user to select and order particular tests based upon the status of the test. The menu bar 248 also includes a "new test" icon 254, a refresh icon 256, a focus icon 258, a "find physician" icon 260 to view scheduled tests and/or test results for patients of a particular physician, an "find patient" icon 262 view scheduled tests and/or test results for a particular patient, a print icon 264, a "home" icon 266, and a "help" icon 268. If the user wishes to obtain specific information about a particular test, the user will activate one of the icons/hyperlinks associated with the particular entry in the window to bring up the "view test" screen 270 as shown in FIG. 12. Alternatively, if the user "right-clicks" on a particular entry, a menu will be provided that allows the user to view the test, edit the test, receive the test, print the test, cancel the test, view the patient's profile and/or view the patient's chart.

The view/edit/new test screen as shown in FIG. 12 provides a scrollable form 272 that allows the user to review, enter and/or modify information related to a particular test that has been, or will be scheduled for a particular patient. If a new test is to be set up, the form 272 will begin as a blank form and the user will enter all of the necessary information to schedule the test. Once entered, this test information will be stored by the CIS in a database 46 and this information will be available by those users of the CIS granted access to such information. Additionally, it is also expected that once the test is set up, a notice will be provided to the physician on the physician dashboard (such as in the clinic inbox 56) that allows the physician to approve the order or the test before it is officially entered on the schedule. Once approved, the patient's chart information is updated.

Figure 13:
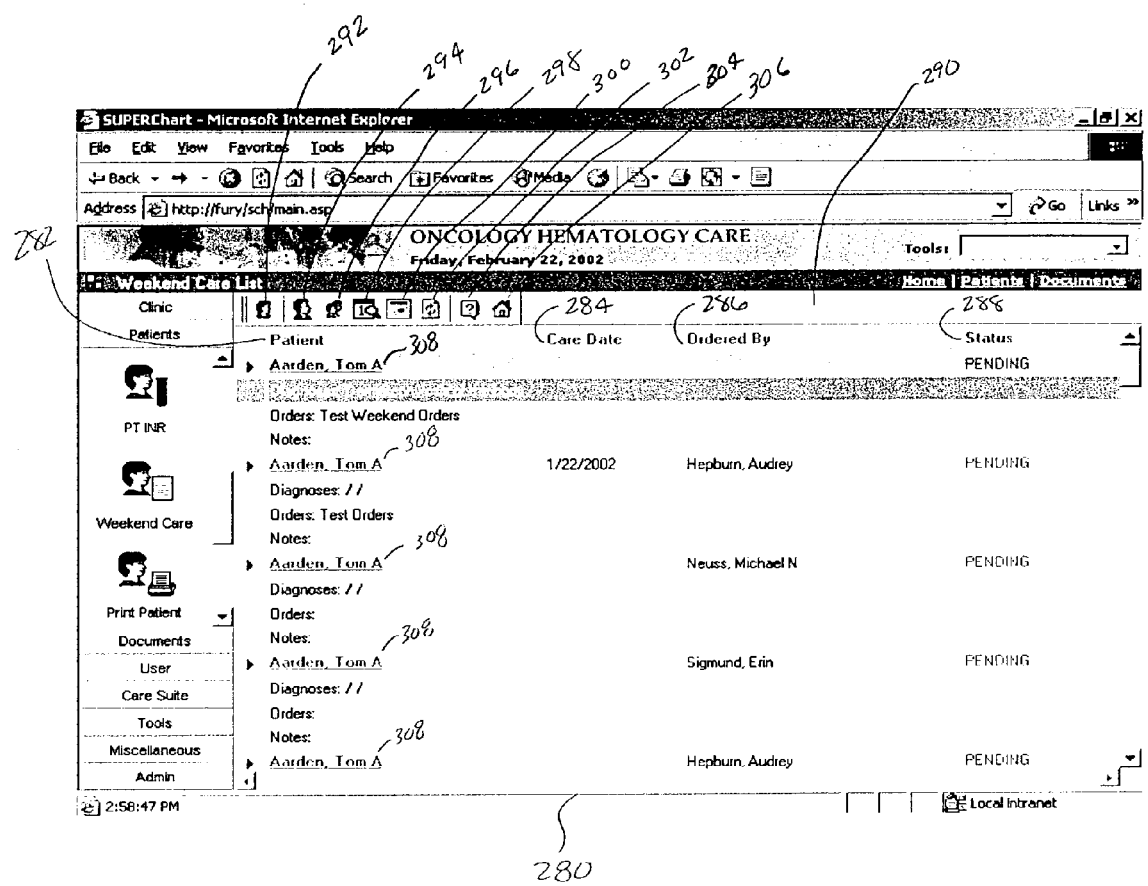
FIG. 13 provides an example weekend care list view screen 280 according to an exemplary embodiment of the present invention.

FIG. 13 provides an example weekend care list view screen 280. The weekend care module organizes care over a weekend for the patient care facility and sets up standing orders applicable over the certain weekend. For example, the weekend care module may be used to schedule chemotherapy over the weekend and standing orders for certain patients/circumstances. The primary window for the weekend care list view screen 280 includes a "Patient" column 282 listing the particular patient set up for weekend care, a diagnosis for the patient, and any standing orders for the weekend and any associated notes; the "Care Date" column 284; the "Ordered By" column 286 indicates the name of the physician ordering the weekend care and the "Status" column 288 provides the status of the weekend care order. The weekend care list view screen 280 also includes a menu bar 290 that includes a "Patient Search" icon 292 and a "Physician" icon 294, a "Weekend Care-Giver" icon 296, a "View Day" icon 298, a "Date-Book" icon 300, a "refresh" icon 302, a "help" icon 304 and a "home" icon 306. In the "Patient" column 282 each patient name listed is a hyperlink 308 that, when activated, brings up the "View Weekend Care" window 310 as shown in FIG. 14.

Figure 14:
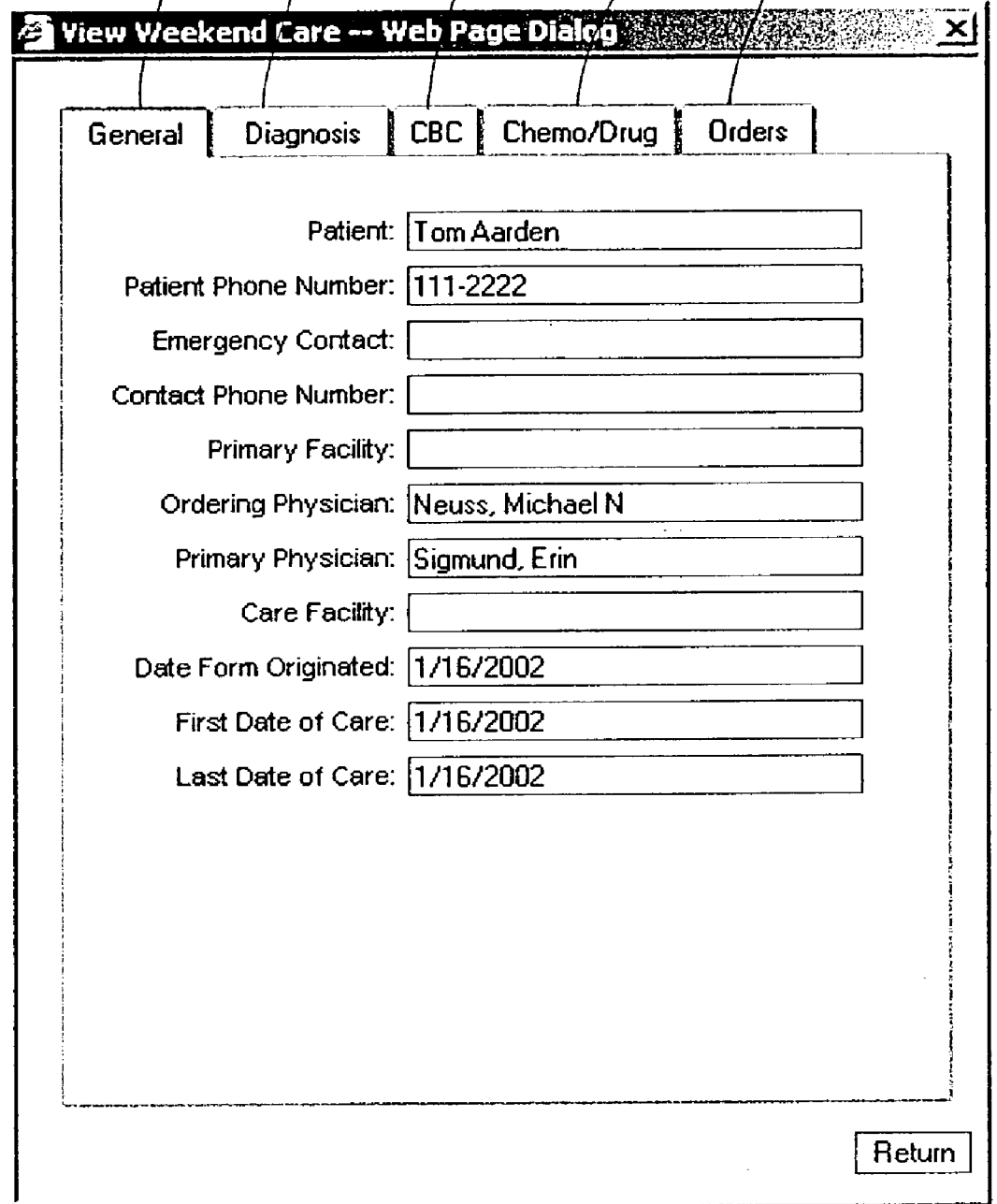
FIG. 14 provides a view-weekend-care dialog form screen 310 according to an exemplary embodiment of the present invention.

As shown in FIG. 14, the View Weekend Care window 310 provides a number of forms, each form being accessible by an associated "tab" including: a general form 312 allowing the user to set up general information for the patient, a diagnosis form 314 allowing the user to set up diagnosis information, a CBC form 316, a chemo/drug form 318 allowing the user to set up the chemotherapy and/or drug schedule for the weekend, and an orders form 320 allowing the user to set up standing orders for the patient on the particular weekend.

Figure 15:
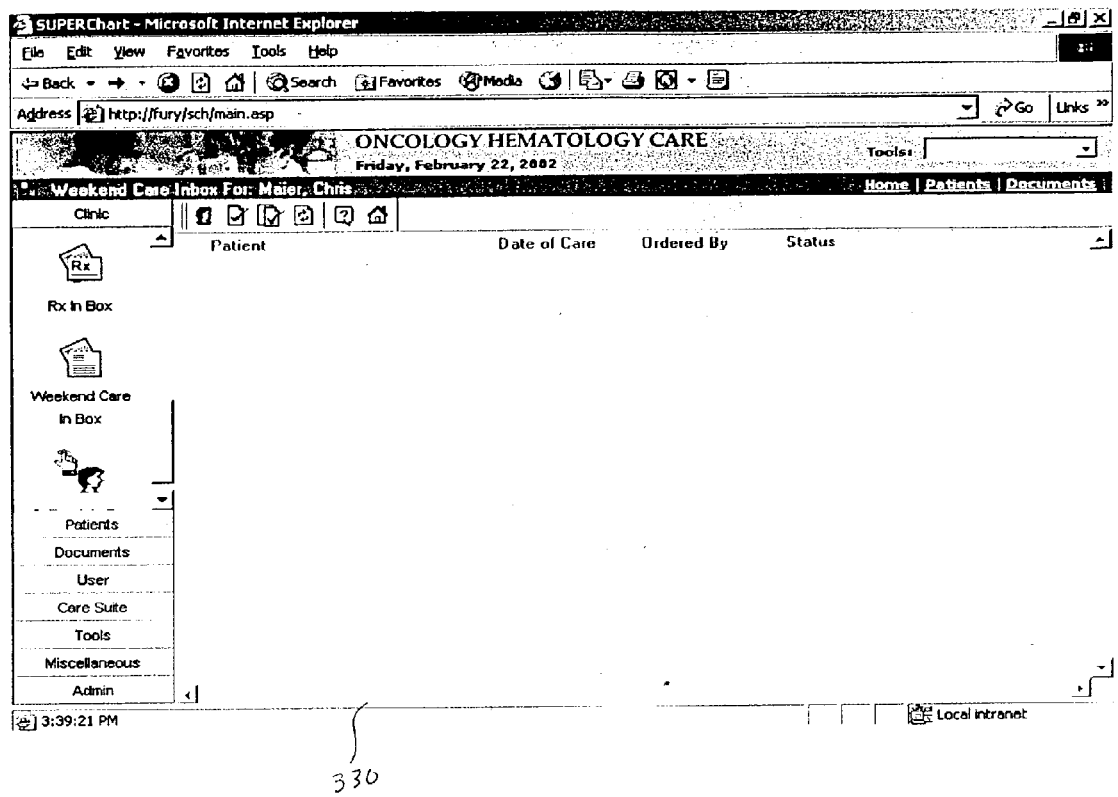
FIG. 15 illustrates an example of a weekend-care in-box screen of a physician's graphical-user-interface according to an exemplary embodiment of the present invention.

FIG. 15 provides an example of a weekend care "Inbox" screen 330 accessible from the physician's dashboard, for example, which allows the physician to review and approve pending "events" over the weekend using the physician's remote computer operatively coupled to the Internet.

Figure 16:
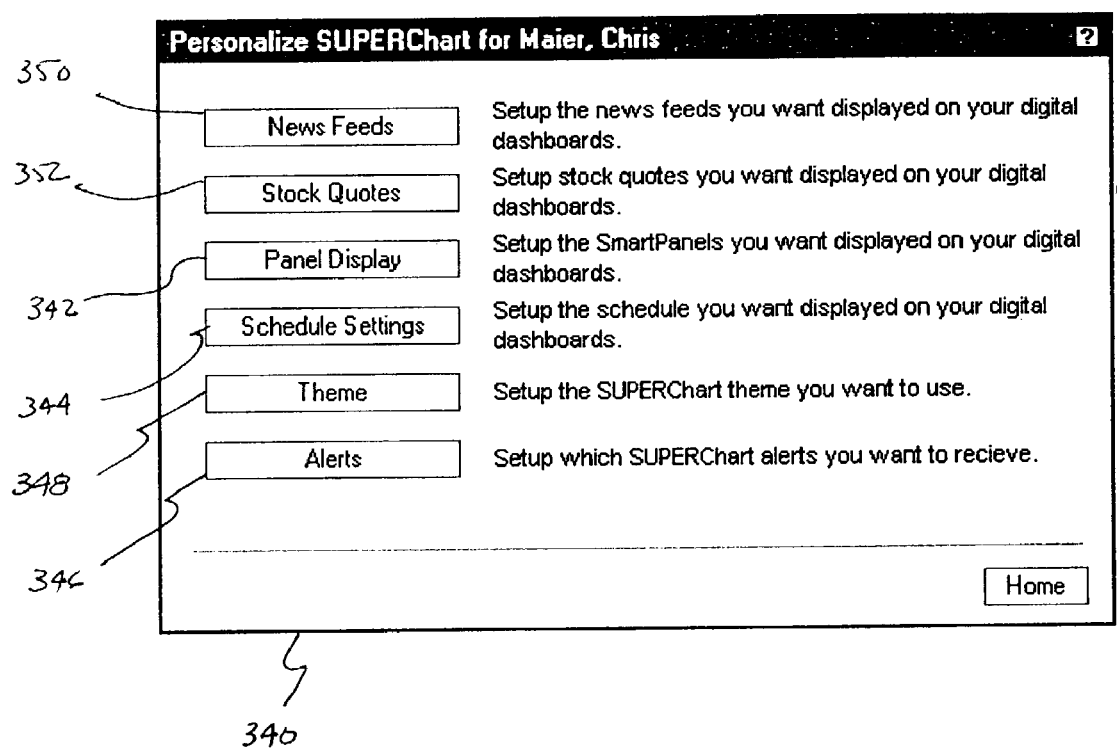
FIG. 16 illustrates an example dashboard personalization tool interface according to an exemplary embodiment of the present invention.

The look, arrangement and contents of each user's digital dashboard is customizable by the user. For example, as shown in FIG. 16, a tool 340 is provided that allows a user to set up the panels or windows on the dashboard by activating icon 342, allows a user to set up the schedules displayed on the dashboard by activating icon 344, allows a user to set up the alerts it wants to receive through the dashboard by activating icon 346, allows a user to set up the theme of the dashboard by activating icon 348, and allows a user to set up news feeds and/or stock quotes to be displayed on the dashboard by activating icons 350 or 352 respectively.

Figure 17:
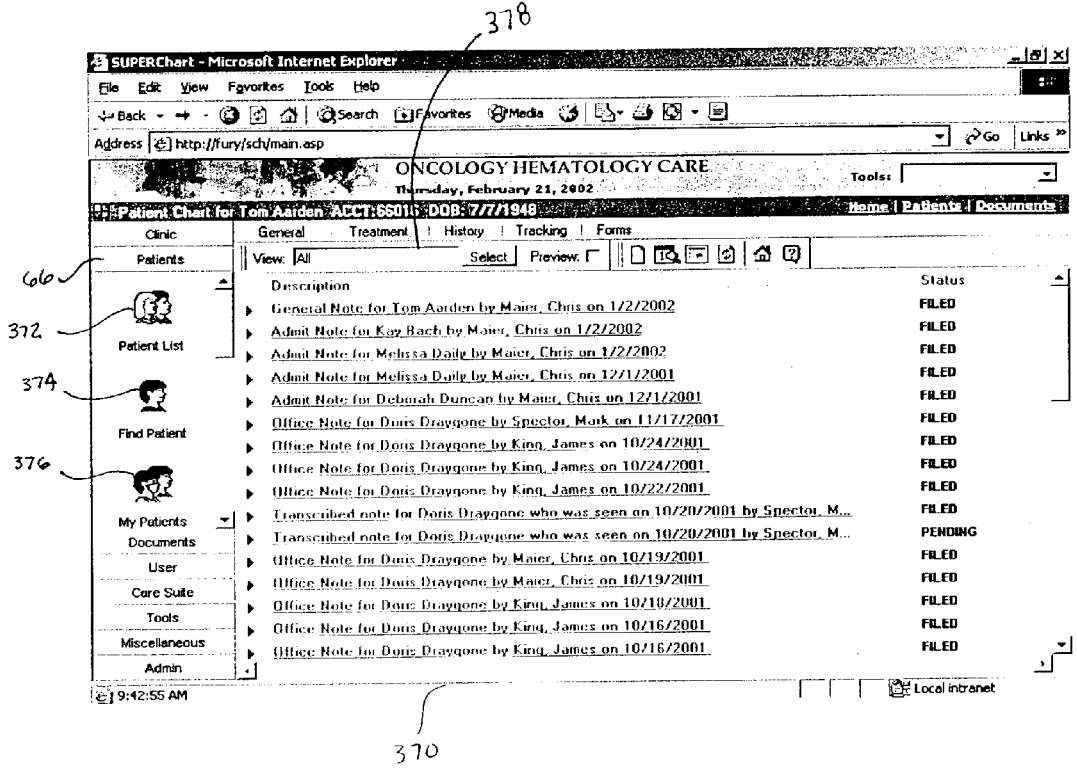
FIG. 17 provides an example patient chart document history screen 370 according to an exemplary embodiment of the present invention.

FIG. 17 provides an example patient chart document history screen 370. The patient chart information can be accessed from the databases 46 by digital dashboards upon an appropriate user activating the "Patients" menu bar 66, for example (see also FIG. 2). Once the "Patients" menu bar is activated a number of functional icons are provided such as: an icon 372 for allowing the user to see a complete patient list, an icon 374 for activating the find-patient search function, and an icon 376 for allowing the physician user to see information for all patients that the physician is responsible. Patient chart information is accessible to most of the various digital dashboards, and because the information is stored in a central database 46, the patient chart information will be consistent to all viewers. The list of patients in this screen 370 may be organized in a number of ways. For example, the list of patients may be organized according to: a particular physician's patients, all patients undergoing a certain study, all patients assigned to certain protocols, all patients on a particular medication or treatment, a global list of patients, etc. Various organizational and filtering options may be selected by the user utilizing the menu field 378, for example.

Figure 18:
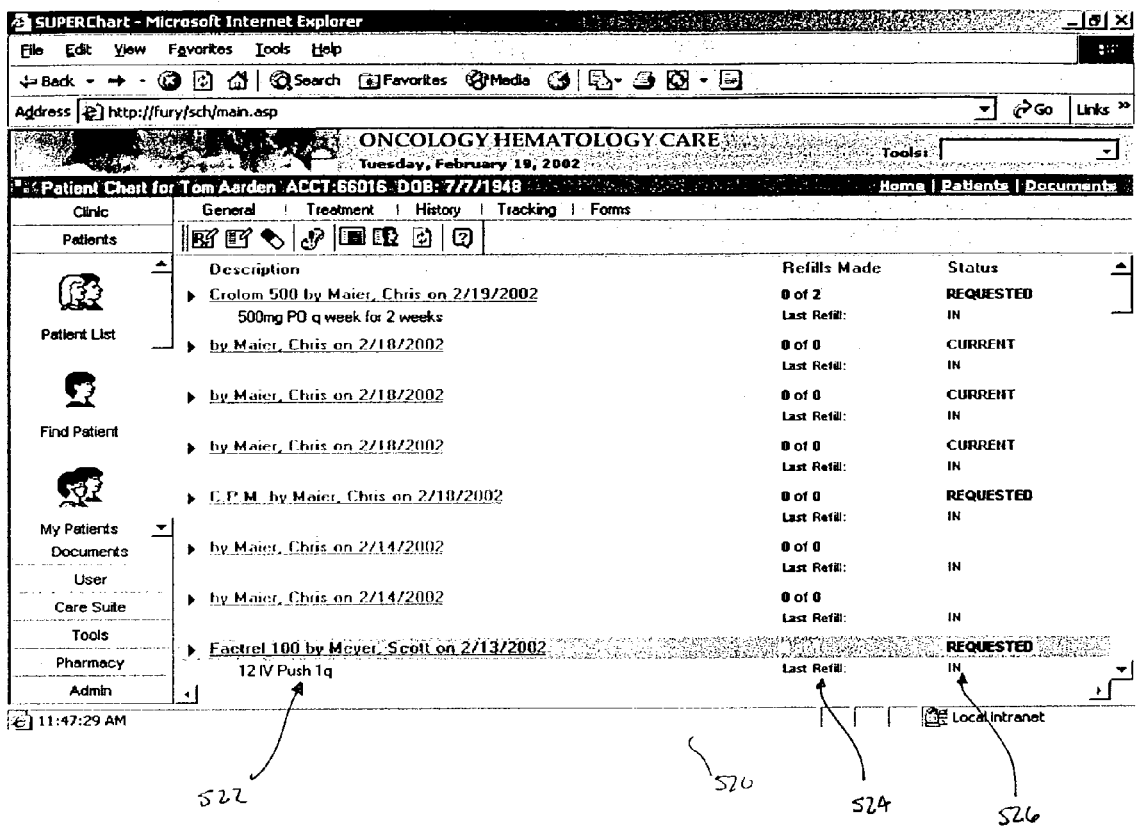
FIG. 18 provides an example patient chart medication history screen 520 according to an exemplary embodiment of the present invention.
Figure 20:
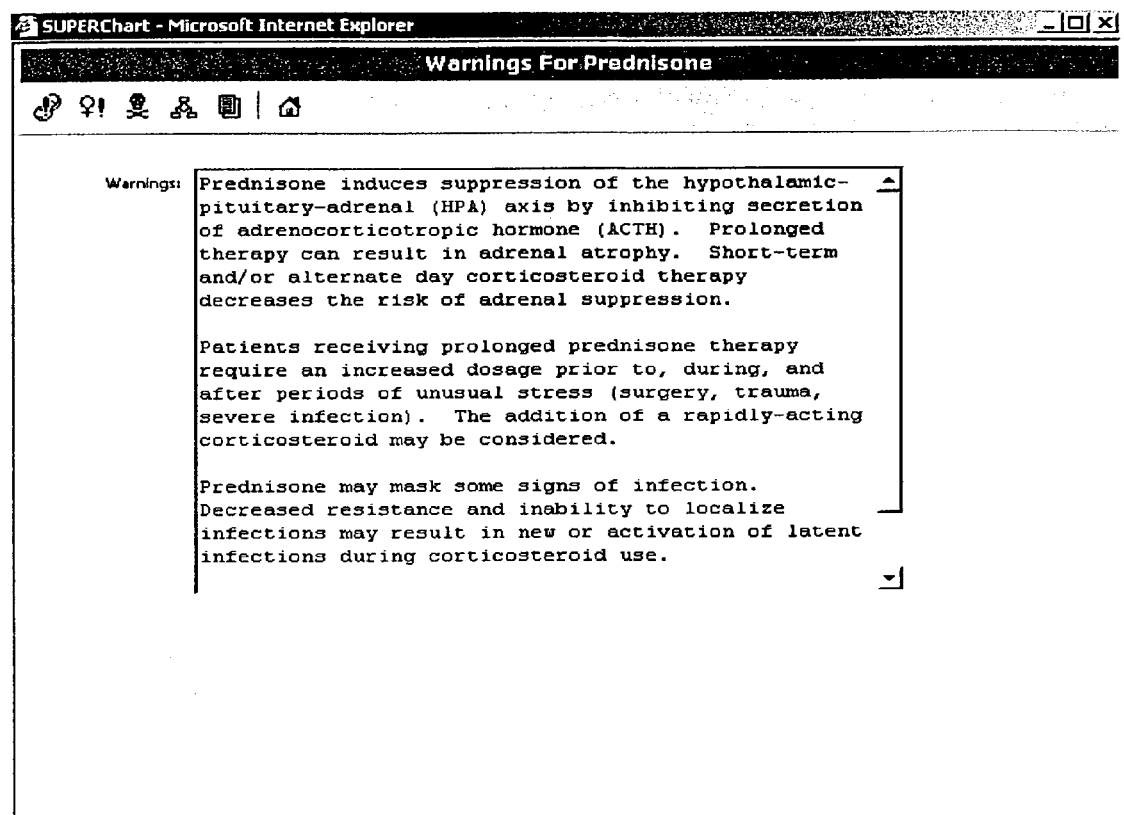
FIG. 20 provides an example drug-warnings screen according to an exemplary embodiment of the present invention.

FIG. 18 provides an example patient chart medication history screen 520. This interface 520 provides a list of medications ordered and/or filled for a particular patient. The list includes a column 522 describing the medication ordered/filled and the physician who ordered/prescribed the medication, a column 524 indicating whether refills have been authorized and/or made, and a column 526 indicating the current status of the order/prescription. From this screen, the CIS also provides a tool where the physician, pharmacists, technicians and the like, for example, can view for possible drug interactions with the medications prescribed or given to a certain patient (See FIGS. 19 and 20). The tool(s) can also check the ordered/prescribed medication against the patient's conditions, allergies, medications and other history to automatically determine if there is a danger or other effect caused by the present order/prescription. Additionally, the tool(s) are configured to the dosage ordered against predetermined minimum/maximum safe dosage levels to automatically determine if there was a mistake made in the dosage entered. Such minimum/maximum safe dosage levels vary for each patient dependent upon, for example, the patient's weight, age, history etc.

It can be seen here that one of the primary advantages of the present invention is that all persons dealing with a patent and/or a patient's chart see the same information (if they are qualified to do so). This ensures better coordination in patient care and improves patient safety.

Figure 21:
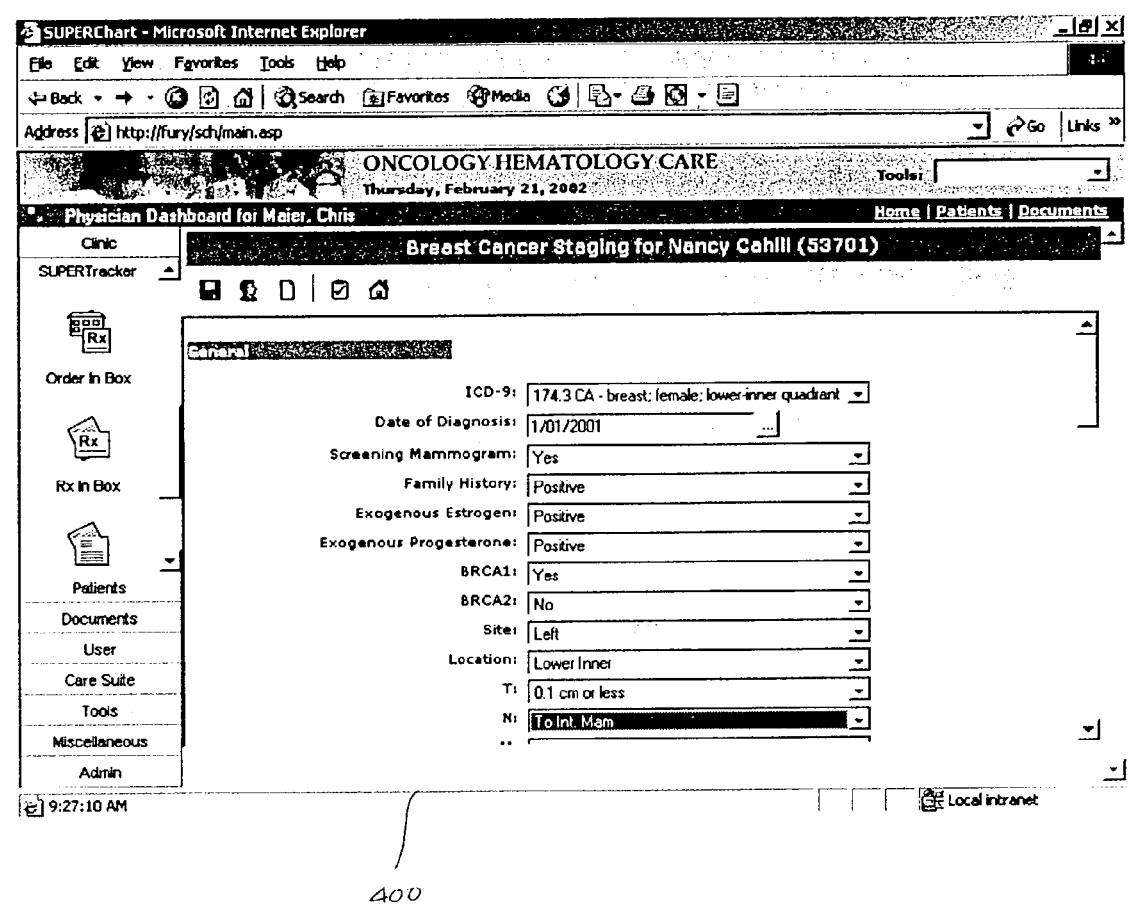
Figure 22:
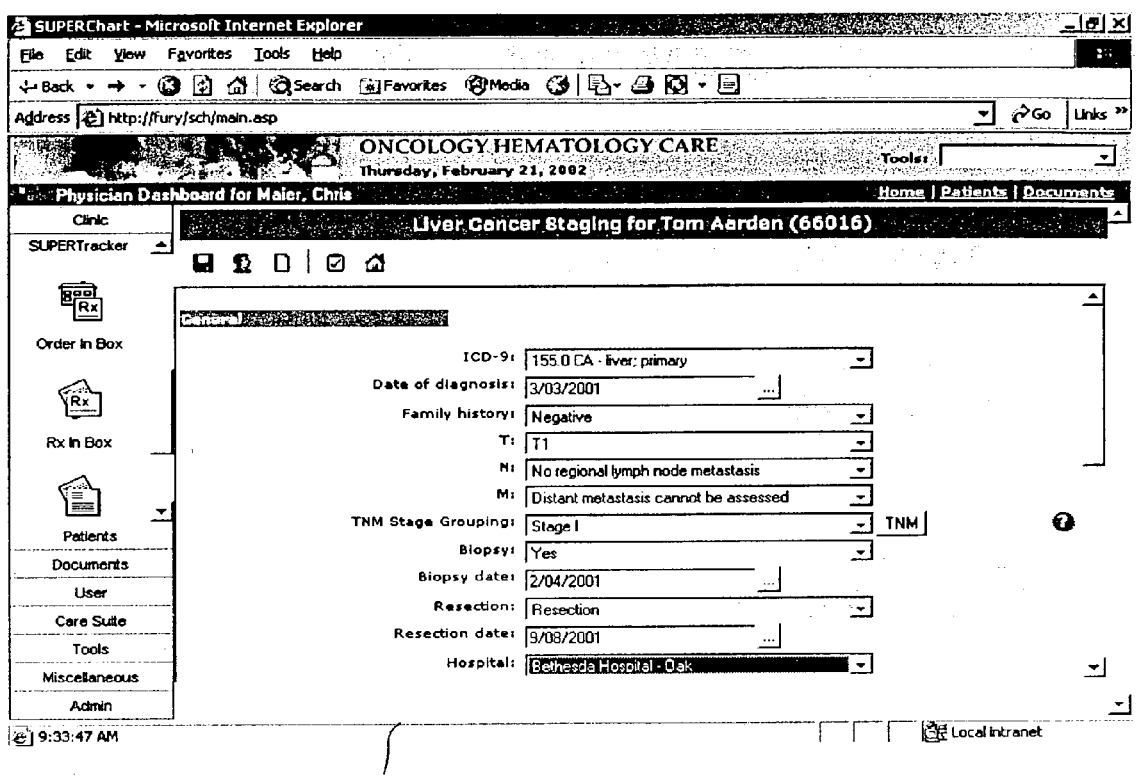
FIG. 22 provides an example form interface for staging liver cancer diagnosis and treatment according to an exemplary embodiment of the present invention.

Referring to FIGS. 21 and 22, the CIS includes a disease staging module that allows a physician or other users to input information into a form 400, 430 related to the stage of a patient's sickness. Such information may include, for example: the present condition and/or diagnosis of the patient, test results, prior medical history of the patient and/or the patient's family, etc. Using this information, the staging module can determine the stage of the patient's disease and can automatically develop a treatment schedule for that patient based upon this determination. For example, different stages of cancer require different treatment programs and schedules. The stage determination is an expert rule-based determination where a set of expert rules are used to assess the information provided in the form (and possibly from other areas) and determine the disease stage based upon the rule set. The CIS is configured such that the rule sets may be initialized upon installation of the CIS in the health-care facility and later customized and/or modified by the health-care facility (preferably by an administrator at the administrator's computer 40) as the disease staging processes are improved and fine-tuned. It is also within the scope of the invention that pre-defined rule sets are provided upon installation, where the health-care facility is able to customize the rule-sets during installation or later as the disease staging processes are improved and fine-tuned.

The requested information in the forms 400, 430 may also be altered and/or customized as the user fills in data based upon the data or information provided. For example, if a field of the form provides a yes/no question, the form may automatically provide custom follow-up requests based upon the answer to the yes/no question, or based upon an answer to a plurality of the fields. Of course, this automatic form handling capability may also be defined by a set of expert rules.

As discussed above, once the disease stage is determined by the staging tool, the staging tool is capable of automatically implementing a treatment program for the patient, where the treatment program may include treatment and medication schedules. Having access to the lab testing and treatment schedules of the health-care facility (and, if necessary, other health-care facilities) in the databases 46 and having access to inventories of available medications/pharmaceuticals in the databases 46, the CIS is able to automatically (or semi-automatically) schedule the treatments/tests and schedule the administration of the various pharmaceuticals during the treatment schedule. Once established, the entire treatment and medication schedules may be automatically sent to the primary physician's digital dashboard for subsequent review, modification and/or approval by the physician. The expert rules for developing the treatment program from the determined disease stage and from other patient information may be customizable by the system administrator as treatments are improved or to conform, for example, to the care facilities policies and procedures.

FIG. 21 provides an example form 400 for staging breast cancer treatment and FIG. 22 provides an example form 430 for staging liver cancer treatment.

Figure 23:
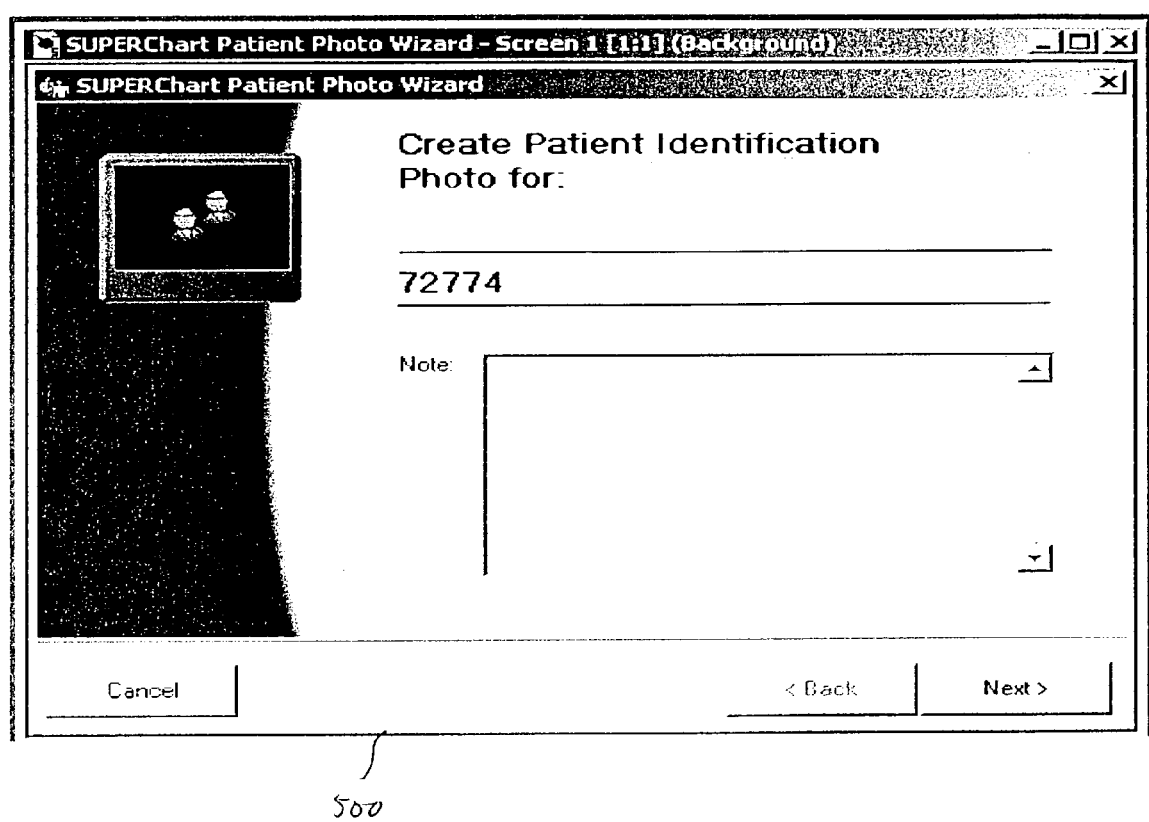
FIG. 23 provides an example photo entry software tool for incorporating digital patient photos into patient records according to an exemplary embodiment of the present invention.

The CIS also provides for the storage of digital photographs of patients in the databases 46 along with the patient's biographical information and charts, etc. These digital photographs may be used for example on the labels of pharmaceuticals and other medications that are to be administered for the patients so that the physician or technician can verify that the proper patient is receiving the pharmaceutical by comparing the digital photograph with the patient's actual appearance. These digital photographs can be used on the patient's printed charts, printed tests, requests, etc. FIG. 23 provides an example "patient photo wizard" 500 for setting up such a digital photograph.

The CIS, in the first exemplary embodiment, is constructed as a tiered, object-based software system. The data inputs into the CIS from all of the various user's computers is controlled by a queued processing. Once an action is requested by a user's computer, the action is places on the queue and the server 30 processes the actions one at a time on a first-in first-out basis. To the particular user, the action appears that it is being processed in real time because the user's screen is updated right away.

Figure 25:
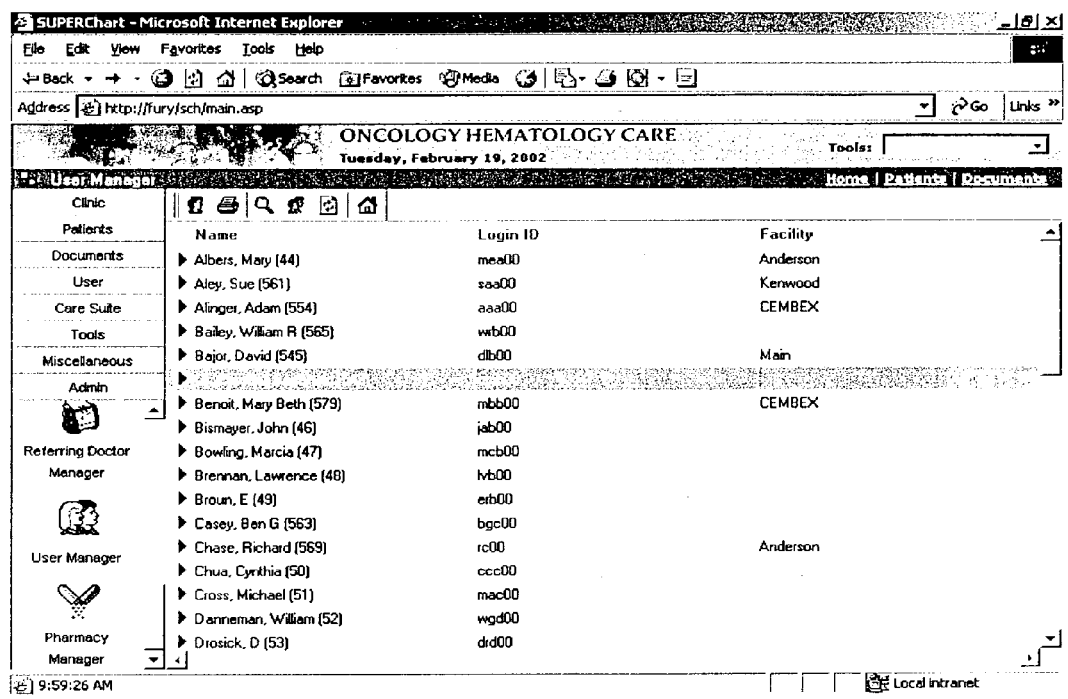
FIG. 25 is an example user-manager administrator's interface screen according to an exemplary embodiment of the present invention.
Figure 26:
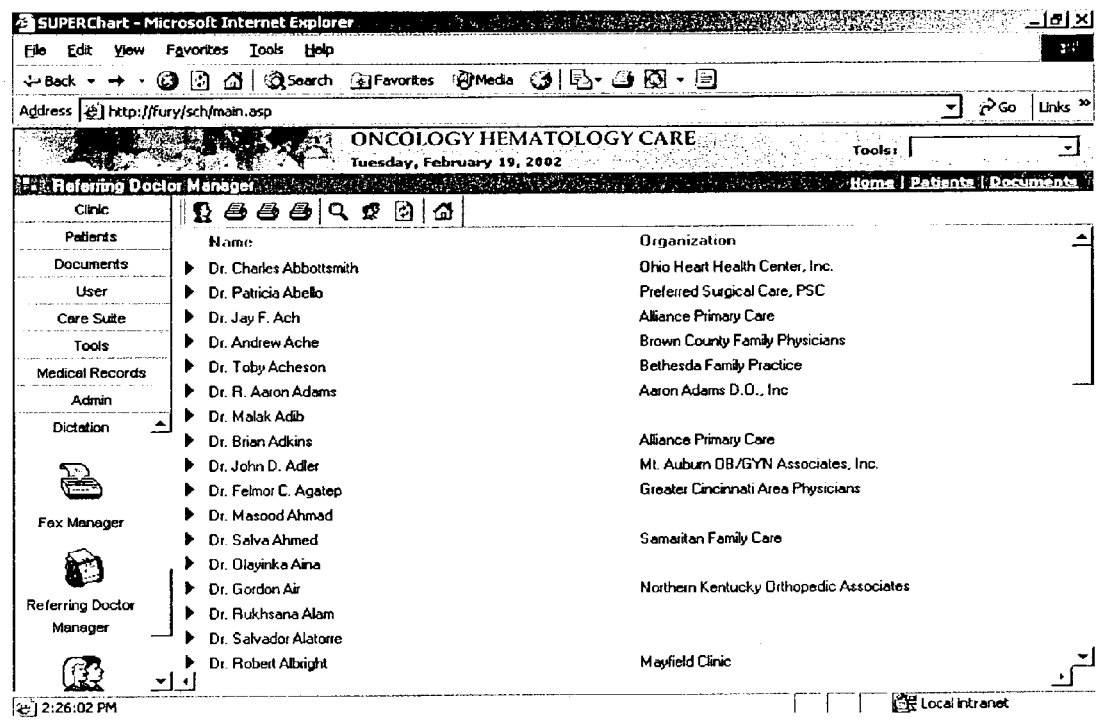
FIG. 26 is an example referring-doctor administrator's interface screen according to an exemplary embodiment of the present invention.
Figure 27:
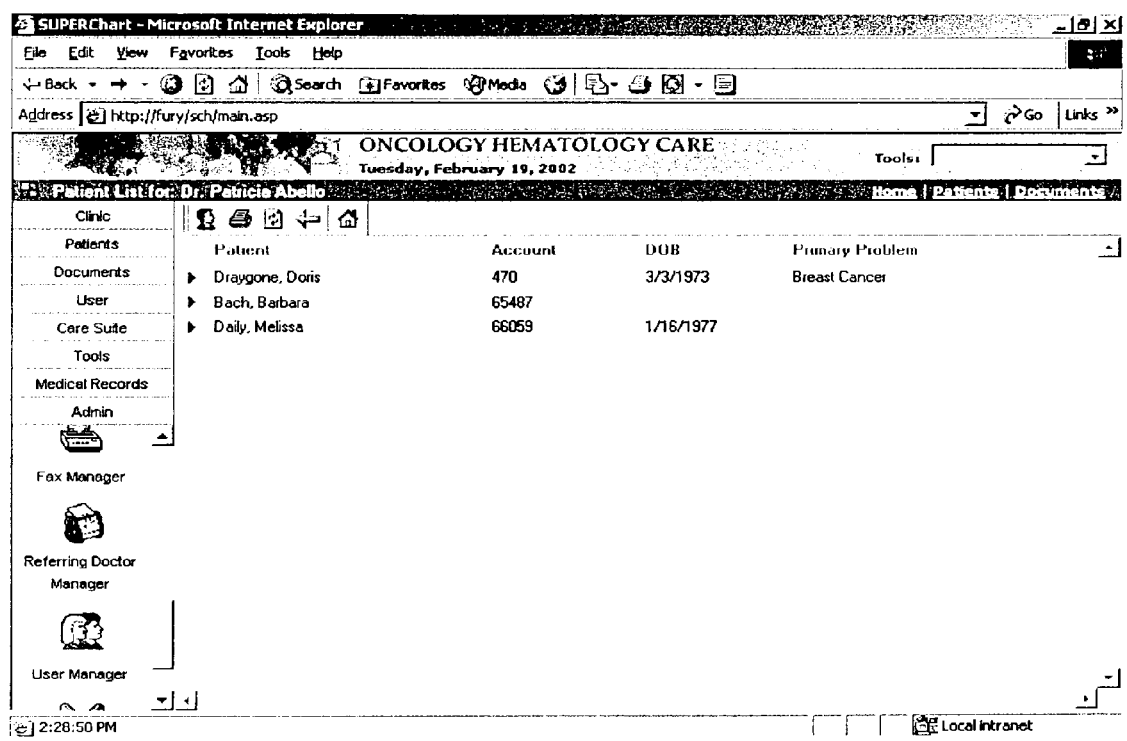
FIG. 27 is an example patient-list-for-referring-doctor administrator's interface screen according to an exemplary embodiment of the present invention.

The operations of the CIS are based upon a set of rules that are preferably customizable by a system administrator. Therefore, the dashboards and other modules, for example, may include or exclude many different types of data or functions as the administrator selects. The administrator is also able to manage the user accounts to the CIS (See FIG. 25, for example), manage the referring doctor information (See FIGS. 26 and 27, for example), and other aspects of the CIS as will be appreciated by those of ordinary skill.

The CIS is also set up with a rules-based Clinical Event Monitor that, for a given medical condition or disease, continuously monitors a patient's chart (for example) for events that have or have not occurred and compares the events against a set of rules set up for the condition/disease. If a discrepancy is detected, the CEM will rout a notification of such to the responsible physician's dashboard/in-box. In detected emergency situations, the CEM can be set up to automatically page the physician for immediate action (have a built-in mechanism to contact the physician's paging service).

The CIS also includes a pharmacy module that is accessible by the pharmacists and technicians on the pharmacy computers 34. The pharmacy module includes its own customized dashboard that provides the pharmacy to generate reports, such as a controlled substance report. The pharmacy dashboard includes an "in-box" listing, for example, the approved pharmaceutical orders from physicians. When generating new pharmacy orders using the New Order Screen, the CIS includes built-in intelligence to automatically check the dosages of the medications/treatments being ordered for safety purposes. For example, the built-in intelligence will have a predefined minimum and maximum dosage for a particular medication or treatment based upon, for example, the patient's body weight and/or condition.

Figure 24:
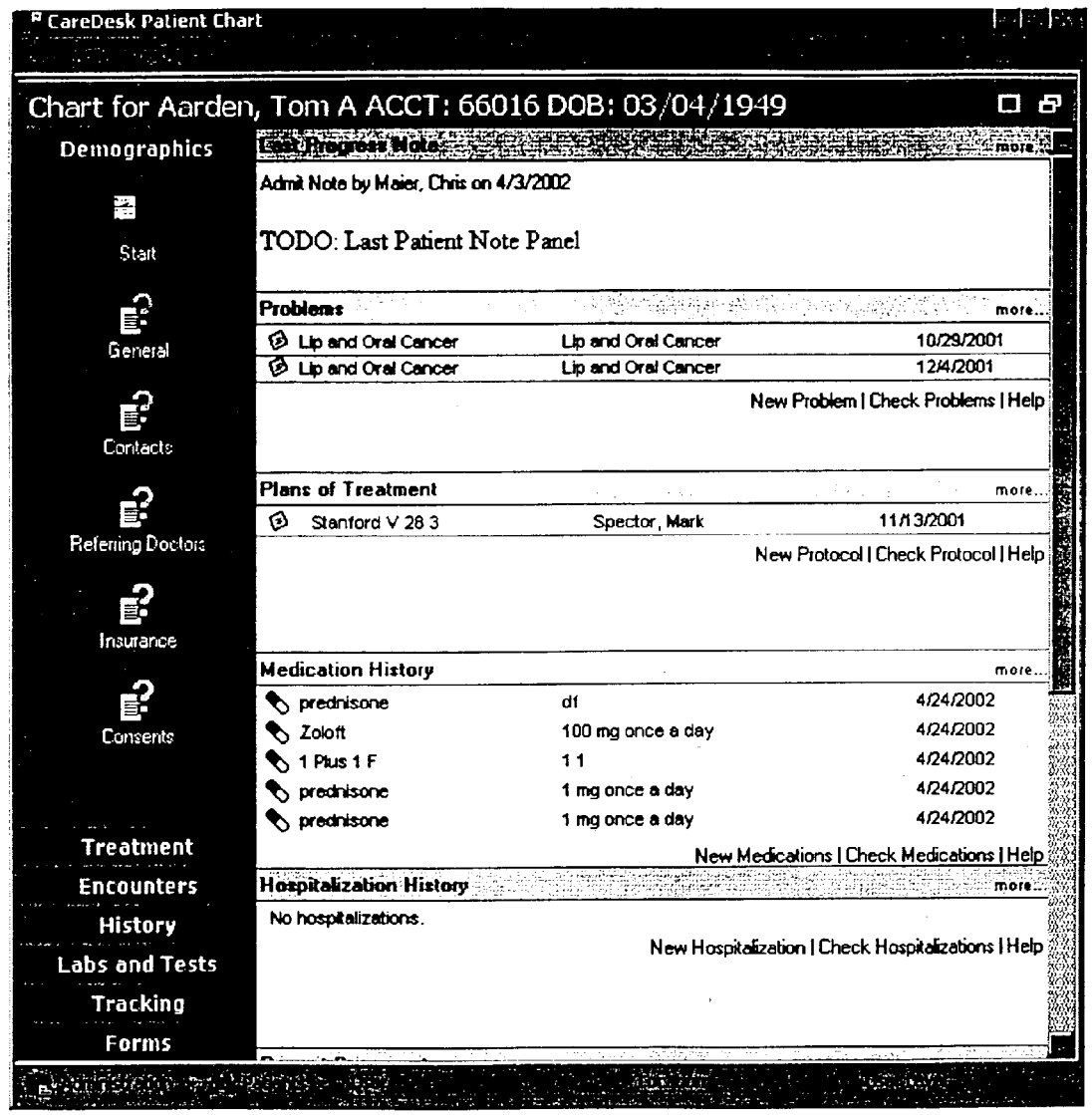
FIG. 24 provides an example patient-medication interface according to a distributed-application embodiment of the present invention.

As discussed above, the second exemplary embodiment of the present invention (referring back to FIG. 2) utilizes dedicated applications installed on the client (user) computers 34-44 that communicate over the Internet (or some other network) 32 to the central server(s) 30 to access/modify the central databases 46 and other centralized information. In the second exemplary embodiment, a distributed application is installed onto the various client (user) computers 34-44, which provides the various functionalities described herein with the first exemplary embodiment, and utilizes Microsoft's NET Web services platform, for example, to access and/or modify the centralized databases 46 and other centralized information from the server(s) 30. The distributed application approach provides much greater flexibility for the invention. For example, with the distributed application approach, it is a simple matter to have multiple windows open at the same time on the user's computer, each of which are sharing data with the Internet simultaneously. Because the distributed application approach no longer needs the use of a browser application, the interfaces will also have a different appearance, although most of the functionality remains the same. FIG. 24, for example, provides a patient chart interface screen for the distributed application embodiment of the invention; and FIG. 28, for example, provides an alternative "view test" screen (performing the same functions as the interface shown in FIG. 12).

Following from the above description and invention summaries, it should be apparent to those of ordinary skill in the art that, while the apparatuses and processes herein described constitute exemplary embodiments of the present invention, it is to be understood that the invention is not limited to these precise apparatuses and processes and that changes may be made therein without departing from the scope of the invention as defined by the claims. Additionally, it is to be understood that the invention is defined by the claims and it is not intended that any limitations or elements describing the exemplary embodiments set forth herein are to be incorporated into the meaning of the claims unless such limitations or elements or explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method for operating a computerized clinical information system for a healthcare facility comprising the steps of:

providing a clinical information system including a plurality of user computers operatively coupled to a global computer network, and at least one computer server operatively coupled to the global computer network, the computer server having access to at least one clinical information memory source, and operative to communicate with the user computers and exchange clinical data between the clinical information memory source and the user computer over the global computer network in a secure manner, each of the user computers operating a software tool allowing a user to view and modify at least certain of the clinical data;

providing an electronic patient chart database on the clinical information memory source, the electronic patient chart database having a plurality of patient chart records;

linking a patient chart record with a primary physician;

logging into the computerized clinical information system using the software tool on a first one of the user computers by a user other than the primary physician;

entering an event for submission to the patient chart record by the user using the software tool on the first one of the user computers;

logging into the computerized clinical information system using the software tool on a second one of the user computers by the primary physician linked with the patient chart record;

in automatic response by the clinical information system to the step of entering the event for submission to the patient chart record, automatically routing the event by the clinical information system to the second one of the user computers in the form of an electronic message for review and approval by the primary physician;

reviewing and approving the event by the primary physician using the software tool on the second one of the user computers; and adding the approved event to the patient chart record;

wherein the software tool on the second one of the user computers provides the primary physician with a graphical user interface that includes a plurality of graphical in-boxes, each of which is designated for a respective category of clinical events associated with the healthcare facility, and the routing step automatically detects a clinical event type for the event and routes the event to a first graphical in-box in the plurality of graphical in-boxes having the designated category associated with the detected clinical event type.

2. The method of claim 1, wherein the event is taken from a group consisting of:
a transcribed document;
a prescription;
an order;
a test result; and
a diagnosis.

3. The method of claim 2, wherein the method includes the step of displaying the event by the graphical user interface on the second one of the user computers in the first graphical in-box for the reviewing and approving step.

4. The method of claim 3, wherein the displaying step includes the step of displaying a plurality of events in the first graphical in-box.

5. The method of claim 3, wherein the graphical user interface on the second one of the user computers includes icons providing access to policies and procedures of the healthcare facility.

6. The method of claim 5, further comprising the steps of:
accessing the policies and procedures of the healthcare facility using the graphical user interface on the second one of the user computers; and
automatically recording information pertaining to the accessing step in an audit database in the clinical information memory source by the clinical information system in automatic response to the accessing step, such recorded information including one or more of the following:
an identity of a user accessing the policies and procedures;
a date of access;
a tune of access;
an identity of the policy or procedure accessed;
whereby such recorded information pertaining to the accessing step can be used to show that such policies and procedures have been reviewed by the primary physician during an accreditation process.

7. The method of claim 1, wherein the plurality of graphical in-boxes include a transcribed document in-box, a prescription in-box, and an order in-box, and the routing step automatically routes events to the transcribed document in-box in response to a detection that the event is a transcribed document automatically routes events to the prescription in-box in response to a detection that the event is a prescription and automatically routes events to the order in-box in response to a detection that the event is an order.

8. The method of claim 7, wherein the plurality of graphical in-boxes further include a test result in-box, and the routing step automatically routes events to the test result in-box in response to a detection that the event is a test result.

9. The method of claim 8, wherein the plurality of graphical in-boxes further include a message in-box, and the routing step automatically routes events to the message in-box in response to a detection that the event is a message.

10. The method of claim 1, wherein the event is a diagnosis and the method further comprises the step of automatically establishing a treatment program by the clinical information system, in automatic response to she approval of the diagnosis by the primary physician in the reviewing and approving step, for the treatment of the diagnosed disease.

11. The method of claim 10, wherein the step of automatically establishing a treatment program further includes the step of automatically establishing a treatment schedule by the clinical information system, in automatic response to the establishment of the treatment program, for implementing the treatment program.

12. The method of claim 11, wherein the clinical information memory source includes a plurality of use schedules for a corresponding plurality of the healthcare facility's resources, and the step of, in automatic response to the establishment of the treatment schedule, automatically establishing the treatment schedule includes the steps of automatically updating the use schedules by the clinical information system to reserve the healthcare facility's resources in accordance with the treatment program.

13. The method of claim 12, wherein the method further includes the step of adding the treatment schedule to the patient chart record.

14. The method of claim 11, wherein the method further includes the step of adding the treatment schedule to the patient chart record.

15. The method of claim 1, wherein information pertaining to the routing, reviewing and approving steps are recorded automatically by the clinical information system in a central audit database, such information including one or more of the following:
   an identity of the user using the software tool on the first one of the user computers;
   a date of entry of the event;
   a time of entry of the event;
   a copy of the event as entered by the user using the software tool on the first one of the user computers;
   an identity of the primary physician;
   a date of approval of the event by the primary physician;
   a time of approval of the event by the primary physician;
   a copy of the event as approved by the primary physician.

16. The method of claim 1, wherein the reviewing and approving steps include the step of modifying the event by the primary physician.

17. The method of claim 16, wherein versions of the event existing before and after the modifying step are stored in a central audit database.

18. The method of claim 1, wherein the electronic message includes a document for consideration by the primary physician, and the method further comprises the step of forwarding, with the assistance of the computerized clinical information system the document to a third party destination.

19. The method of claim 1, wherein the electronic message includes a document for consideration by the primary physician, and the method further comprises the step of faxing, with the assistance of the computerized clinical information system, the document to a third party.

20. A method for operating a computerized clinical information system for a healthcare facility comprising the steps of:
   providing a clinical information system including a plurality of user computers operatively coupled to a global computer network, end at least one computer server operatively coupled to the global computer network, the computer server having access to at least one clinical information memory source, and operative to communicate with the user computers and exchange clinical data between the clinical information memory source and the user computer over the global computer network in a secure manner, each of the user computers operating a software tool allowing a user to view and modify at least certain of the clinical data, the clinical information memory source includes a plurality of use schedules for a corresponding plurality of the healthcare facility's resources;
   providing an electronic patient chart database on the clinical information memory source, the electronic patient chart database having a plurality of patient chart records and a plurality of use schedules for a corresponding plurality of the healthcare facility's resources;
   linking a patient chart record with a primary physician;
   logging into the computerized clinical information system using the software tool on a first one of the user computers by a user other than the primary physician;
   entering a diagnosis for submission to the patient chart record by the user using the software tool on the first one of the user computers;
   logging into the computerized clinical information system using the software tool on a second one of the user computers by the primary physician linked with the patient chart record;
   automatically renting the diagnosis by the clinical information system to the second one of the user computers in the form of an electronic message for review and approval by the primary physician;
   reviewing and approving the diagnosis by the primary physician using the software tool on the second one of the user computers;
   adding the approved diagnosis to the patient chart record;
   automatically establishing a treatment program by the clinical information system for the treatment of the diagnosed disease;
   automatically establishing a treatment schedule by the clinical information system for implementing the treatment program; and
   automatically checking the use schedules for openings by the clinical information system and automatically filling openings in the use schedules by the clinical information system according to the treatment program;
   wherein the software tool an the second one of the user computers provides the second one of the user computers with a graphical user interface that includes a plurality of graphical in boxes, each of which is designated for a respective category of clinical events associated with the healthcare facility, and the routing step automatically detects a clinical event type for the diagnosis and routes the diagnosis to a first graphical in-box in the plurality of graphical in-boxes having the designated category associated with the detected clinical event time.

21. A method for operating a computerized clinical information system for a healthcare facility comprising the steps of:
   providing a clinical information system including a plurality of user computers operatively coupled to a global computer network, and at least one computer server operatively coupled to the global computer network, the computer server having access to at least one clinical information memory source, and operative to communicate with the user computers and exchange clinical data between the clinical information memory source and the user computer over the global computer network in a secure manner, each of the user computers operating a software tool allowing a user to view and modify at least certain of the clinical data, the clinical information memory source includes a plurality of use schedules for a corresponding plurality of the healthcare facility's resources;

providing an electronic patient chart database on the clinical information memory source, the electronic patient chart database having a plurality of patient chart records and a plurality of use schedules for a corresponding plurality of the healthcare facility's resources;

automatically linking a patient chart record with a primary physician;

logging into the computerized clinical information system using the software tool on a first one of the user computers by a user other than the primary physician;

entering a diagnosis for submission to the patient chart record by the user using the software tool on the first one of the user computers;

logging into the computerized clinical information system using the software tool on a second one of the user computers by the primary physician linked with the patient chart record;

automatically routing the diagnosis by the clinical information system to the second one of the user computers in the form of an electronic message for review and approval by the primary physician;

reviewing and approving the diagnosis by the primary physician using the software tool on the second one of the user computers;

adding the approved diagnosis to the patient chart record;

automatically establishing a treatment program by the clinical information system for the treatment of the diagnosed disease;

automatically establishing a treatment schedule by the clinical information system for implementing the treatment program; and automatically establishing a medication schedule by the clinical information system according to the treatment program;

wherein the software tool on the second one of the user computers provides the second one of the user computers with graphical user interface that includes a plurality of graphical in-boxes, each of which is designated for a respective category of clinical events associated with the healthcare facility, and the routing step automatically detects a clinical event type for the diagnosis and routes the diagnosis to a first graphical in-box in the plurality of graphical in-boxes having the designated category associated with the detected clinical event type.

22. The method of claim 21, wherein the clinical information memory source includes a medication inventory for the healthcare facility and the step of automatically establishing a medication schedule includes the step of automatically updating the medication inventory by the clinical information system in automatic response to the establishment of the medication schedule.

23. The method of claim 22, wherein the method further includes the step of adding the treatment schedule to the patient chart record.

24. A method for operating a computerized clinical information system for a healthcare facility comprising the steps of:

providing a clinical information system including a plurality of user computers operatively coupled to a global computer network, and at least one computer server operatively coupled to the global computer network, the computer server having access to at least one clinical information memory source, and operative to communicate with the user computers and exchange clinical data between the clinical information memory source and the user computer over the global computer network in a secure manner, each of the user computers operating a soft-ware tool allowing a user to view and modify at least certain of the clinical data;

providing an electronic patient chart database on the clinical information memory source, the electronic patient chart database having a plurality of patient chart records and a plurality of use schedules for a corresponding plurality of the healthcare facility's resources;

linking a patient chart record with a primary physician;

logging into the computerized clinical information system using the software tool on a first one of the user computers by a user other than the primary physician;

entering a diagnosis for submission to the patient chart record by the user using the software tool on the first one of the user computers;

logging into the computerized clinical information system using the software tool on a second one of the user computers by the primary physician linked with the patient chart record;

automatically routing the diagnosis by the clinical information system to the second one of the user computers in the form of an electronic message for review and approval by the primary physician;

reviewing and approving the diagnosis by the primary physician using the software tool on the second one of the user computers;

adding the approved diagnosis to the record; and automatically establishing a treatment program by the clinical information system for the treatment of the diagnosed disease, the step of automatically establishing a treatment program for the treatment of the diagnosed disease includes the step of automatically applying a set of electronically stored expert rules against the diagnosed disease byte clinical information system;

wherein the software tool on the second one of the user computers provides the second one of the user computers with a graphical user interface that includes a plurality of graphical in-boxes, each of which is designated for a respective category of clinical events associated with the healthcare facility, and the routing step automatically detects a clinical event type for the diagnosis and routes the diagnosis to a first graphical in-box in the plurality of graphical in-boxes having the designated category associated with the detected clinical event type.

25. The method of claim 24, wherein the diagnosed disease includes a stage of the diagnosed disease.

26. A method for operating a computerized clinical information system for a healthcare facility comprising the steps of:

providing a clinical information system including a plurality of user computers operatively coupled to a global computer network, and at least one computer sewer operatively coupled to the global computer network, the computer server having access to at least one clinical information memory source, and operative to communicate with the user computers and exchange clinical data between the clinical information memory source and the useR computer over the global computer network in a secure manner, each of the user computers operating a software tool allowing a user to view and modify at east certain of the clinical data;

providing an electronic patient chart database on the clinical information memory source, the electronic patient chart database having a plurality of patient chart records and a plurality of use schedules for a corresponding plurality of the healthcare facility's resources;

linking a patient chart record with a primary physician;

logging into the computerized clinical information system using the software tool on a first one of the user computers by a user other than primary physician;

entering a diagnosis for submission to the patient chart record by the user using the software tool on the first one of the user computers;

logging into the computerized clinical information system using the software tool on a second one of the user computers by the primary physician linked with the patient chart record;

automatically routing the diagnosis by the clinical information system to the second one of the user computers in the form of an electronic message for review and approval by the primary physician;

reviewing and approving the diagnosis by the primary physician using the software tool on the second one of the user computers; and adding the approved diagnosis to the patient chart record; and automatically establishing a treatment program by the clinical information system for the treatment of the diagnosed disease;

wherein the diagnosed disease includes a stage of the diagnosed disease and the method further comprises the steps of:

providing a disease staging software tool on one of the user computers, wherein the disease staging software tool includes a plurality of condition fields pertaining to diagnosed or recorded conditions of a patient and includes a set of expert rules for determining a stage of the disease based upon the diagnosed or recorded conditions of the patient;

completing the condition fields on the disease staging software tool by a user on the one of the user computers; and automatically processing the completed condition fields against the set of expert rules by the clinical information system to determine the stage of the disease in response to the step of completing the condition fields on the disease staging software tool by the user on the one of the user computers;

wherein the step of automatically establishing a treatment program by the clinical information system for the treatment of the diagnosed disease, automatically establishes a treatment program according to the determined stage of the disease; and wherein the software tool on the second one of the user computers provides the second one of the user computers with a graphical user interface that includes a plurality of graphical in-boxes, each of which is designated for a respective category of clinical events associated with the healthcare facility, and the routing step automatically detects a clinical event type for the diagnosis and routes the diagnosis to a first graphical in-box in the plurality of graphical in-boxes having the designated category associated with the detected clinical event type.

27. A method for operating a computerized clinical information system for a healthcare facility comprising the steps of:

providing a clinical information system including a plurality of user computers operatively coupled to a global computer network, and at least one computer server operatively coupled to the global computer network, the computer server having access to at least one clinical information memory source, and operative to communicate with the user computers and exchange clinical data between the clinical information memory source and the user computers over the global computer network in a secure manner, each of the user computers operating a software tool allowing a user to view and modify at least certain of the clinical data;

providing an electronic patient chart database on the clinical information memory source, the electronic patient chart database having a plurality of patient chart records;

linking a patient chart record with a primary physician;

logging into the computerized clinical information system using the software tool on a first one of the user computers by a user taken from a group consisting of a pharmacist, a pharmacy technician, a nurse, a non-primary physician and a pharmacy assistant;

entering at least one request taken from a group consisting of a new prescription and an order for approval by the primary physician by the user using the software tool on the fast one of the user computers;

in automatic response to the entering of the new prescription or order, automatically checking a requested dosage of the new prescription or order against safety guidelines by the clinical information system;

logging into the computerized clinical information system using the software tool on a second one of the user computers by the primary physician;

automatically routing the request to the second one of the user computers in the form of an electronic message for review and approval by the primary physician;

reviewing and approving the request by the primary physician using the software tool on the second one of the user computers; and adding the approved request to the patient chart record;

wherein the soft-ware tool on the second one of the user computers provides the primary physician with a graphical user interface that includes a plurality of graphical in-boxes, each of which is designated for a respective category of clinical events associated with the healthcare facility, and the routing step automatically detects a clinical event type for the request and routes the request to a first graphical in-box in the plurality of graphical in-boxes having the designated category associated with the detected clinical event type.

28. The method of claim 27, wherein the step of automatically checking a requested dosage of the new prescription or order against safety guidelines includes the step of automatically providing a minimum and maximum dosage for at least one of a patient's body weight and a patient's of condition by the clinical information system in automatic response to the entering of the new prescription or order.

* * * * *